United States Patent [19]

Edwards et al.

[11] Patent Number: 5,681,308
[45] Date of Patent: *Oct. 28, 1997

[54] ABLATION APPARATUS FOR CARDIAC CHAMBERS

[75] Inventors: Stuart D. Edwards, 1681 Austin Ave., Los Altos, Calif. 94024; Hugh R. Sharkey, Redwood Shores, Calif.

[73] Assignee: Stuart D. Edwards, Los Altos, Calif.

[*] Notice: The term of this patent shall not extend beyond the expiration date of Pat. No. 5,505,730.

[21] Appl. No.: 345,142

[22] Filed: Nov. 28, 1994

Related U.S. Application Data

[63] Continuation-in-part of Ser. No. 319,373, Oct. 6, 1994, Pat. No. 5,575,788, which is a continuation-in-part of Ser. No. 286,862, Aug. 4, 1994, Pat. No. 5,558,672, which is a continuation-in-part of Ser. No. 272,162, Jul. 7, 1994, Pat. No. 5,569,241, which is a continuation-in-part of Ser. No. 265,459, Jun. 24, 1994, Pat. No. 5,505,730.

[51] Int. Cl.$^6$ ...................................................... A61B 17/39
[52] U.S. Cl. .............................. 606/41; 606/28; 606/192; 606/193; 604/21; 607/101; 607/102
[58] Field of Search ................................. 606/27–34, 41, 606/42, 45–50, 191–193; 607/98–102; 604/53, 96–102, 21, 22

[56] References Cited

U.S. PATENT DOCUMENTS

| | | |
|---|---|---|
| 1,620,929 | 3/1927 | Wallerich . |
| 1,827,306 | 10/1931 | Chapman et al. . |
| 3,645,265 | 2/1972 | Majzlin . |
| 3,840,016 | 10/1974 | Lindemann . |
| 3,924,628 | 12/1975 | Droegemueller et al. . |
| 3,948,270 | 4/1976 | Hasson . |
| 4,057,063 | 11/1977 | Gieles et al. . |
| 4,676,258 | 6/1987 | Inokuchi et al. . |
| 4,799,479 | 1/1989 | Spears ........................................ 606/28 |
| 4,865,047 | 9/1989 | Chou et al. . |
| 4,949,718 | 8/1990 | Neuwirth et al. . |
| 4,960,133 | 10/1990 | Hewson . |
| 4,961,435 | 10/1990 | Kitagawa et al. . |

(List continued on next page.)

OTHER PUBLICATIONS

Singer et al., "Preliminary Clinical Experience With A Thermal Balloon Endometrial Ablation Method To treat Menorrhagia", *Obstetrics & Gynecology*, vol. 83, No. 5, Part 1, pp. 732–734, May 1994.

Phipps et al., "Treatment of Functional Menorrhagia By Radiofrequency–Induced Thermal Endometrial Ablation", *The Lancet*, United Kingdom, vol. 335, pp. 374–376, Feb. 17, 1990.

(List continued on next page.)

*Primary Examiner*—Jennifer Bahr
*Assistant Examiner*—Michael Peffley
*Attorney, Agent, or Firm*—Fliesler, Dubb, Meyer & Lovejoy

[57] ABSTRACT

An endocardial ablation and mapping apparatus is introduced into a heart chamber for mapping to detect arrhythmogenic foci, and ablate endocardium at the arrhythmogenic foci. An inflatable, flexible porous membrane is adapted to receive an electrolytic solution, and become inflated to substantially conform a conductive surface of the membrane to the wall of the heart chamber. A membrane support is surrounded by the membrane, and includes a sealed proximal end and a sealed distal end. Each end has an aperture formed therein defining a central lumen in the membrane support that permits blood flow through the support member and the heart chamber. The membrane support is attached to the membrane and is expanded to a non-distensible state when the membrane is inflated. A catheter, with a distal end, is attached to the membrane or the membrane support. The membrane and membrane support are introduced into the heart chamber by the catheter in a non-expanded state, and become expanded to an expanded state by inflating the membrane with the electrolytic solution. A plurality of treatment electrodes, defining a circuit, are formed on an exterior surface of the membrane support. An RF power source is coupled to the treatment electrodes, and a source of electrolytic solution is coupled to the membrane.

54 Claims, 16 Drawing Sheets

U.S. PATENT DOCUMENTS

| | | |
|---|---|---|
| 4,979,948 | 12/1990 | Geddes et al. . |
| 5,084,044 | 1/1992 | Quint . |
| 5,151,100 | 9/1992 | Abele et al. ............................ 606/28 |
| 5,156,151 | 10/1992 | Imran . |
| 5,186,181 | 2/1993 | Franconi et al. . |
| 5,188,122 | 2/1993 | Phipps et al. . |
| 5,191,883 | 3/1993 | Lennox et al. . |
| 5,228,442 | 7/1993 | Imran . |
| 5,232,444 | 8/1993 | Just et al. ............................ 604/96 |
| 5,236,413 | 8/1993 | Feiring . |
| 5,255,697 | 10/1993 | Grauer . |
| 5,263,493 | 11/1993 | Avitall . |
| 5,277,201 | 1/1994 | Stern ............................ 607/98 |
| 5,279,299 | 1/1994 | Imran . |
| 5,311,866 | 5/1994 | Kagen et al. . |
| 5,344,402 | 9/1994 | Crocker ............................ 604/96 |
| 5,505,730 | 4/1996 | Edwards et al. ............................ 606/41 |

OTHER PUBLICATIONS

Phipps et al., "Experimental and Clinical Studies With Radiofrequency—Induces Thermal Endometrial Ablation For Functional Menorrhagia", *Obstetrics & Gynecology*, United Kingdom, vol. 76, No. 5, Part 1, pp. 876–881, Nov. 1990.

Prior et al., "Treatment of Menorrhagia By Radiofrequency Heating", *Int. J. Hyperthermia*, United Kingdom, vol. 7, No. 1, 22–230, pp. 213–216, 1991.

Mumford et al., "Sterilization Needs in the 1990's: The Case For Quinacrine Nonsurgical Female Sterilization", *American Journal of Obstetrics & Gynecology*, United Kingdom, vol. 167, No. 5, pp. 1203–1207, Nov. 1992.

Neuwirth et al., "The Endometrial Ablator: A New Instrument", *Obstetrics & Gynecology*, vol. 83, No. 5, Part 1, pp. 792–796, May 1994.

ABLATION APPARATUS FOR CARDIAC CHAMBERS

CROSS-REFERENCE TO RELATED APPLICATIONS

This application is a continuation-in-part of U.S. patent application Ser. No. 08/319,373 entitled "Thin Layer Ablation Apparatus" by Baker et al, filed Oct. 6, 1994, now U.S. Pat. No. 5,575,788, which is a continuation-in-part of U.S. patent application Ser. No. 08/286,862 entitled "Thin Layer Ablation Apparatus" by Edwards et al, filed Aug. 4, 1994, now U.S. Pat. No. 5,558,672, which is a continuation-in-part of U.S. patent application Ser. No. 08/272,162 entitled "Thin Layer Ablation Apparatus" by Edwards, et al, filed Jul. 7, 1994, now U.S. Pat. No. 5,569,241, which is a continuation-in-part of U.S. patent application Ser. No. 08/265,459 entitled "Thin Layer Ablation Apparatus" by Edwards filed Jun. 24, 1994, now U.S. Pat. No. 5,505,730, all of which are incorporated by reference.

BACKGROUND OF THE INVENTION

1. Field of the Invention

This invention relates to an ablation and mapping apparatus for use in the field of cardiac arrhythmia, and more particularly, to an apparatus for treating atrial fibrillation.

2. Description of Related Art

The Sino Atrial ("SA") node provides impulses which control the normal rhythmic contractions of the heart atria and the ventricles. This involves the transmission of the normal cardiac conduction pathways in the atria, and the ventricles, which cause the heart to contract and relax in an orderly sequence at a rate set by the SA node.

A depolarization impulse begins with the SA node, and spreads as an electrical wave in the SA node in the right atrium to the left atrium, and down toward the lower chambers of the heart. At the junction of the atria and the ventricles there is another node, known as the atrioventricular (AV) node. The impulse is conducted through the AV node in a slower fashion so as to coordinate the mechanical function of the atria and ventricles. The impulse continues to a common pathway, known as the bundle of HIS, between the right and left ventricles, and then into the Purkinje system and into multiple paths, the right and left bundle branches, each bundle branch supplying one ventricle. Each bundle branch divides into an extensive network of finer paths of conducting tissue which spread from the inner to the outer surfaces of the heart, and which are referred to as the Purkinje fibers. These fibers conduct the depolarization impulse into all portions of the ventricular myocardium.

As long as this depolarization impulse system is intact, impulses are transmitted normally and cardiac rhythm is maintained. There are sometimes variations from the normal rhythm of the heart beat which are manifested as abnormal spontaneous contractions or as rapid re-entrant impulses that dangerously speed the heart rhythm (tachycardia). These abnormalities are clinically referred to as arrhythmias, and they can cause numerous unwanted and potentially dangerous complications for patients.

The arrhythmogenic foci of an arrhythmia is most often located in the endocardium and initiates the arrhythmia. Since heart muscle contractions result from the progression of an excitation wave of electrical impulses, location of the arrhythmogenic foci is accomplished by identifying the point from where the abnormal excitation wave originates by the use of intra cardiac mapping.

Ventricular tachycardia (VT) and other ventricular arrhythmias have been treated with a number of drugs such as lidocaine, quinidine, aminodrone and procainamide. Beta blocking drugs have also been used. In cases where drug therapy has been ineffective in preventing tacharrhythmias, certain surgical procedures have been used to ablate the reentry path either with the atria or the ventricles.

One procedure involves extensive surgery via thoracotomy with an incision through the pericardium and heart muscle. The arrhythmogenic foci is located, frozen or surgically removed. The surgical procedures utilize either a hand held electrical mapping probe or a computerized array of electrodes that are placed on the endocardium (inner wall) or the epicardium (outside wall) of the heart, acquiring electrical activation data to identify the site of origin of the arrhythmia.

Open heart surgery procedures are high risk and require a prolonged period of hospitalization and recuperation. Less traumatic solutions have been developed. Catheters of various types have been developed and used for diagnosing and treating a number of cardiac abnormalities to avoid the trauma of open heart surgery. In percutaneous catheter procedures, a catheter with recording electrodes is positioned in the heart under fluoroscopic guidance. Following acquisition of electrical activation data, ablation energy is then delivered by hand held probes or catheters either in the operating room or in the cardiac catheterization lab.

Catheters have been proposed to map the arrhythmogenic foci. Such catheters are disclosed in U.S. Pat. Nos. 5,156,151; 5,255,697; 5,228,442; 5,263,493 and 5,279,299. However, these catheters fail to provide for the identification, isolation and quick instruction to treat arrhythmogenic fool. The successful use of radio frequency (RF) energy to eliminate VT requires an accurate pace map of the earliest local endocardial activation and firm catheter contact with the endocardium.

For patients with coronary artery disease, the failure to eliminate VT using RF energy delivered through a catheter has been hypothesized to be due to the small size and shallow depth of the lesion created by RF energy, preventing it from reaching subendocardial (or deeper) regions of the head. Additional contributing factors may also include inaccurate mapping in scarred ventricles or a location of the arrhythmogenic foci at sites deep to the endocardium. There has been successful elimination of idiopathic, usually right ventricular, VT in patients without structural heart disease with direct current countershocks. Complications, such as trauma and risk of ventricular perforation, associated with direct current countershocks make this technique less desirable unless very low energies are used.

It would be desirable to provide an ablation apparatus which is inserted into a heart chamber, such as an atrium, expanded from a folded configuration by the introduction of an electrolytic solution into a microporous membrane surrounding a membrane support, identifies and localizes the arrhythmogenic foci, and then very quickly instructs an energy delivery source to treat the arrhythmogenic foci. There is a need to treat arrhythmogenic foci deep in the endocardium without the treatment electrodes lying in direct physical contact with the head wall. It would be desirable to provide a cardiac ablation apparatus which provides ablation depths suitable to effectively treat the arrhythmogenic foci (transmurally across the muscular wall of the heart), including an ability to reach the subendocardial, or deeper, region of the heart.

SUMMARY

Accordingly, an object of the present invention is to provide a cardiac ablation apparatus which provides a plurality of treatment electrode segments for the controlled ablation of the endocardium with the ability to reach transmural regions of the heart muscle.

Another object of the present invention is to provide a cardiac ablation apparatus which provides an expandable member, such as a microporous membrane, surrounding a membrane support, permitting blood to flow through an interior lumen of the membrane support.

A further object of the present invention is to provide a cardiac ablation apparatus which positions the treatment electrodes on an outside surface of a membrane support so that there is no direct contact between the treatment electrodes and the endocardium.

Yet another object of the present invention is to provide a cardiac ablation apparatus which provides an electrolytic solution delivered through the microporous membrane to the endocardium for improved ablation.

Another object of the invention is to provide a cardiac ablation apparatus which includes a microporous membrane, membrane support and treatment electrodes positioned on at outside surface of the membrane support.

Still another object of the invention is to provide a cardiac ablation apparatus which includes a microporous membrane, membrane support, treatment electrodes positioned on at outside surface of the membrane support, and a plurality of MAP electrodes positioned on a conductive surface of the membrane.

A further object of the invention is to provide a cardiac ablation apparatus which provides a flexible circuit of treatment electrodes with segments that can be multiplexed.

Yet another object of the present invention is to provide a cardiac ablation and mapping apparatus that includes a microporous membrane in direct contact with the endocardium, and resources to map the heart in order to seek the origin of the arrhythmia, identify early local endocardial activation, and then ablate the arrhythmogenic foci.

These and other objects of the invention are provided in an endocardial mapping and ablation apparatus that is introduced into a heart chamber, particularly an atrium, to treat atrial fibrillation. An inflatable, flexible porous membrane is adapted to receive an electrolytic solution and become inflated to substantially conform a conductive surface of the membrane to the wall of the heart chamber. A membrane support is surrounded by the membrane. The membrane support includes a sealed proximal end, and a sealed distal end, each end having an aperture formed therein defining a central lumen in the membrane support that permits blood flow through the support member and heart chamber. The membrane support is attached to the membrane and is expanded to a non-distensible state when the membrane is inflated. A catheter, with a distal end, is attached to the membrane or the membrane support. The membrane and membrane support are introduced into the heart chamber by the catheter in a non-expanded state, and become expanded to an expanded state by inflating the membrane with the electrolytic solution. The electrolytic solution can be delivered through the catheter. As the membrane becomes inflated, it pulls the membrane support to the non-distensible state. A plurality of treatment electrodes, defining a circuit, are formed on an exterior surface of the membrane support. MAP electrodes are positioned on an exterior surface of a conductive surface of the membrane. An RF power source is coupled to the treatment electrodes, and a source of electrolytic solution is coupled to the membrane.

In another embodiment of the invention, the plurality of treatment electrodes is supported between the membrane support and the surrounding membrane. At least some of the plurality of treatment electrodes include an insulator formed on a surface of the treatment electrode adjacent to the membrane. The insulator is partially deposited on the treatment electrodes so that a back side of the membrane is insulated from the direct delivery of RF energy from that treatment electrode. The insulator prevents RF energy from passing directly through the membrane. Instead, RF energy is applied indirectly to the endocardium, causing a thermal effect to the tissue. RF energy from the treatment electrodes arcs out through the membrane. The membrane support can serve as an additional insulator.

The ablation apparatus further includes electrical resources for acquiring electrical data from the heart and providing electrical function feedback to the RF generator which then supplies a therapeutic output to the plurality of treatment electrodes in response to the electrical data. Both the membrane and membrane support include a plurality of adjacently positioned blood flow apertures. These apertures permit blood to flow through the right atrium at an inlet of the superior vena cava, an inlet of the inferior vena cava, and at the tricuspid annulus. A ground pad can be attached to an exterior surface of a patient. Additionally, the apparatus can be operated in a bipolar mode.

Hoops, rings, and the like, generally referred to as attachment members, are positioned on a catheter distal end and attach to the membrane or membrane support. After the procedure is completed, the membrane and membrane support are rolled around the catheter distal end for removal from the heart chamber.

A conductive surface of the membrane, e.g., the surface located adjacent to the endocardium, can be coated with an anti-coagulating material. A deposition of ions can be included in the membrane to improve RF and thermal energy conductivity.

The treatment electrodes can also be positioned in an interior of the membrane. In this embodiment, the treatment electrodes are in a spaced apart relationship from the membrane's conductive surface so that there is no direct contact between the treatment electrodes and the endocardium.

The treatment electrodes can form a flexible circuit, with associated thermocouples. Individual treatment electrodes are treated as segments in the flexible circuit. These segments can be multiplexed. Ablation of the endocardium can be at a desired level, including the subendocardium and deeper, based on the detected characteristic of the arrhythmogenic foci. The deeper it is, then more RF energy is applied by the respective treatment electrode or segment.

The present invention provides mapping and detection of the arrhythmogenic foci, ablation at the appropriate depth, and subsequent re-mapping. Blood flow in the heart chamber is substantially uninterrupted.

DETAILED DESCRIPTION OF THE PREFERRED EMBODIMENTS

The present invention provides a cardiac ablation and mapping system which includes a cardiac ablation and mapping apparatus. Cardiac ablation and mapping apparatus includes a microporous membrane, surrounding a membrane support, a plurality of RF treatment electrodes that are positioned on an exterior surface of the membrane support, and a plurality of MAP electrodes positioned on an exterior surface of the membrane. The membrane is made of a material that permits it to closely conform to the wall of the heart, and is expandable by introducing an electrolytic solution through it. The ablation apparatus is introduced into a selected heart chamber in a non-expanded configuration. It is introduced in a folded or rolled configuration around a distal end of a catheter. Once the ablation apparatus is positioned in the desired heart chamber, it is then expanded. This expansion occurs when electrolytic solution is introduced into the membrane which is made of a material that permits it to closely conform to the wall of the heart. The treatment electrodes are not in direct contact with the heart wall. MAP electrodes and electrical resources are included to map the heart to acquire electrical activation data to seek the origin of the arrhythmia, provide early local endocardium activation and electrical function feedback to an RF generator, and then provide a therapeutic output to the treatment electrodes in order to ablate the arrhythmogenic foci.

Figure 1:
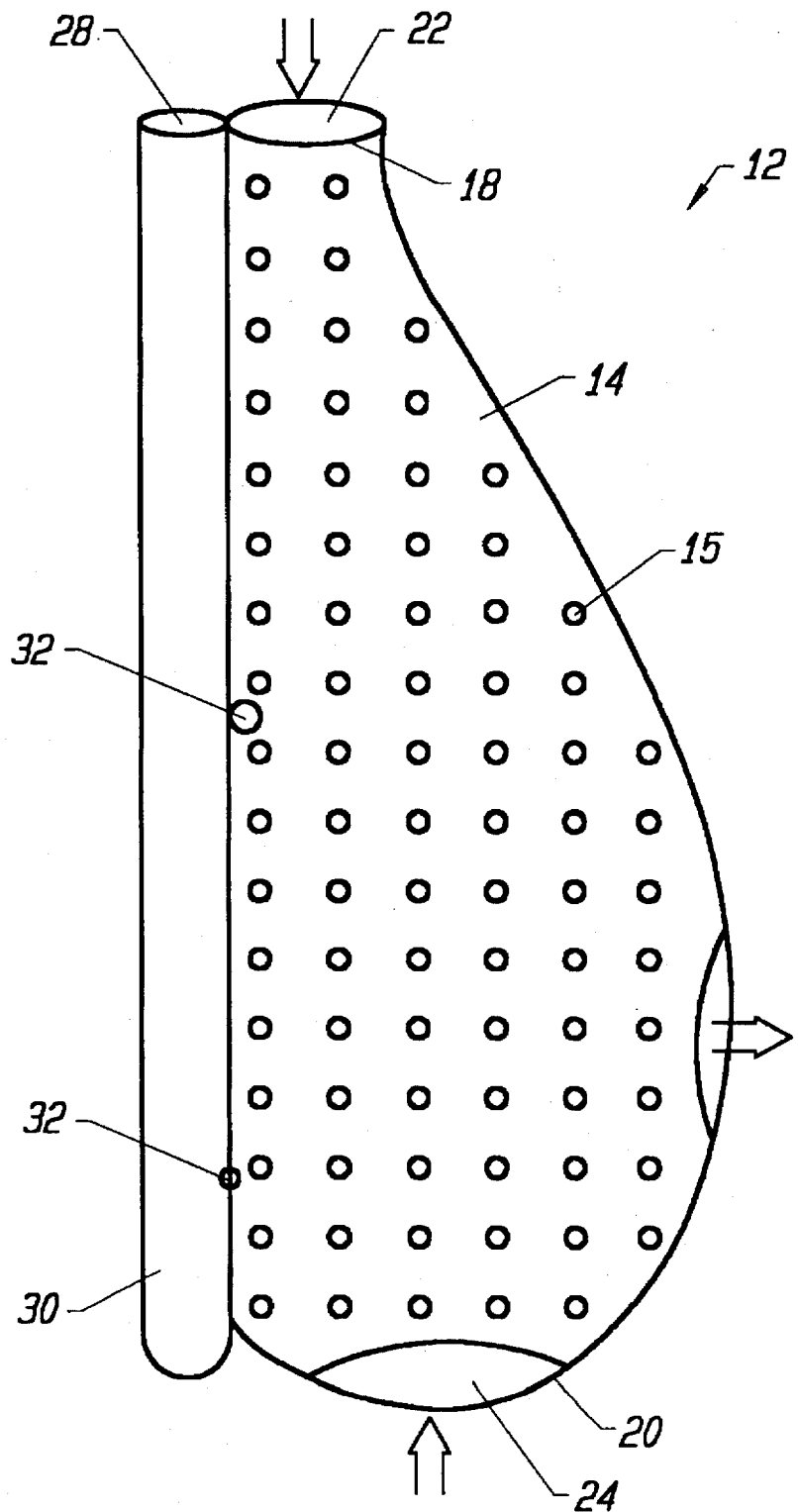
FIG. 1 is a cross-sectional view of the cardiac ablation and mapping apparatus of the invention.
Figures 2, 3:
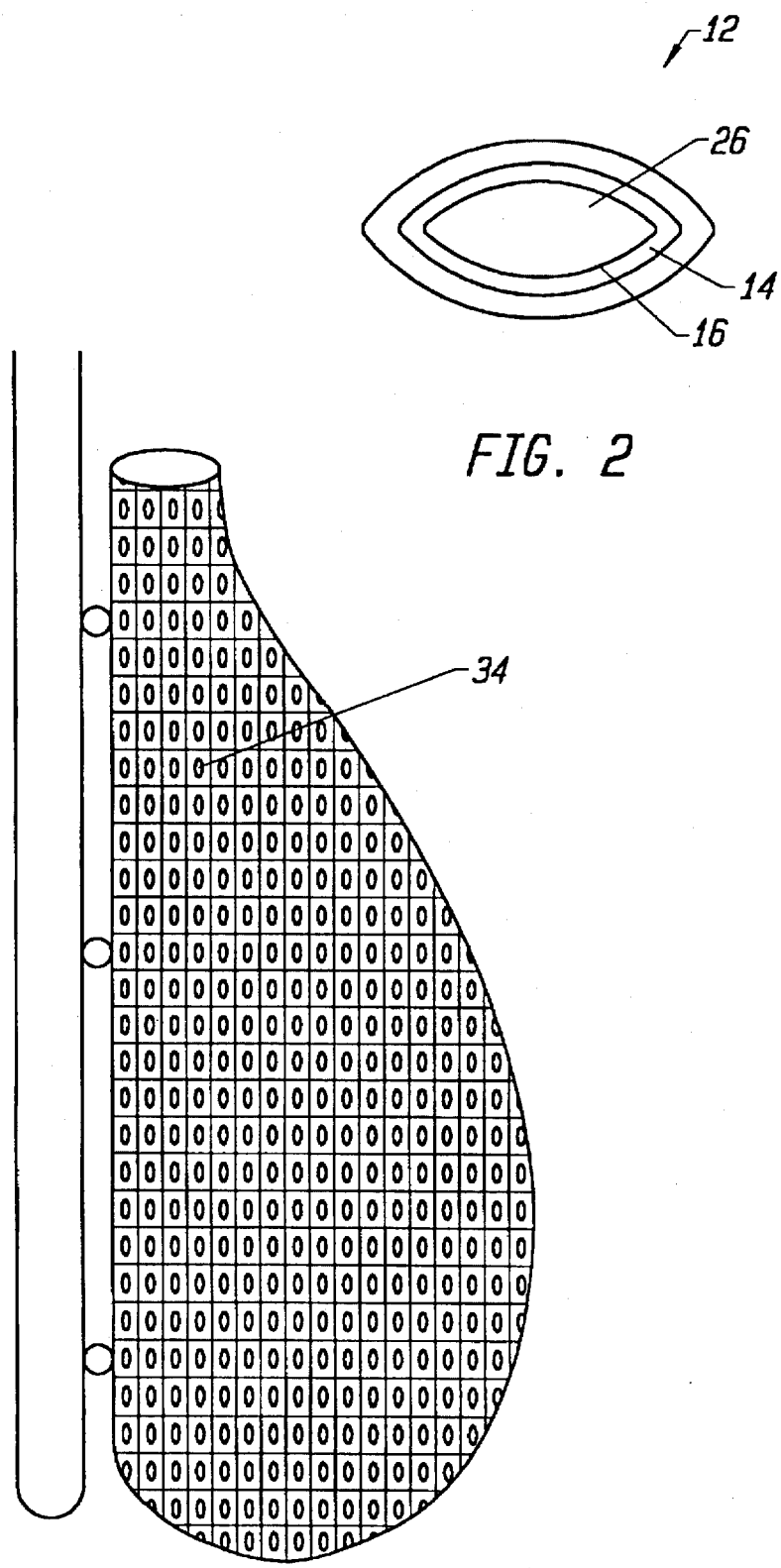
FIG. 2 is a cross-sectional view of the ablation and mapping apparatus of FIG. 1.
FIG. 3 is a perspective view of an exterior wall of the membrane support of the invention, with the electrodes positioned on the exterior wall.

Referring now to FIGS. 1 and 2, cardiac ablation and mapping system 10, particularly suitable for the right atrium, and includes a cardiac ablation and mapping apparatus 12. Ablation apparatus 12 includes a porous membrane 14 which surrounds a membrane support 16. Membrane support 16 provides a separation of membrane 14 and electrolytic solution from a flow of blood through a lumen formed in membrane support 16, as more fully explained hereafter. Membrane 14 can be of the microporous type and be made of Mylar, expanded PFT such as Gortex available from Gore Company, and the like. Membrane 14 is relatively strong, and sufficiently heat resistant for the amount of thermal energy that is supplied to the endocardium. The flow rate of electrolytic solution through membrane 14 is determined by, (i) the pomposity of membrane 14 and (ii) the introduction rate of the electrolytic solution to membrane 14. A plurality of MAP electrodes 15 are positioned on an exterior surface of membrane 14. MAP electrodes 15 can be monophasic action potential electrodes, comprised of a silver, silver chloride matrix that can be either deposited on the surface of membrane 14. Alternatively, MAP electrodes 15 can be an independent electrode that is placed on the outside surface of membrane 14, usually centered so that it has a very low impedance characteristic.

Membrane 14 substantially surrounds membrane support 16. Membrane support 16 includes a sealed proximal end 18 and a sealed distal end 20. It will be appreciated that ends 18 and 20 can include wing like structures that are configured to be positioned next to the associated vein or valve, to more readily introduce ablation apparatus and position it properly in the left or right atrium. Each of the ends 18 and 20 include an aperture 22 and 24 respectively, formed therein, defining a central lumen 26 which extends in a general longitudinal direction through membrane support 16, permitting blood to flow through membrane support 16 and the heart chamber. Membrane support 16 is attached to membrane 14 and is expanded to a non-distensible state when membrane 14 is inflated.

A catheter 28, with a distal end 30, is attached to membrane 14 or membrane support 16 with attachment devices including but not limited to hooks, loops and the like. Catheter 28 may be a combination of a latex/silicon rubber composite that has a non-pliable, non-flexible, inner show or glove. Catheter 28 also serves as a "spine" for ablation apparatus 12. Membrane 14 and membrane support 16 are initially in a folded or rolled type of basket, non-expanded configuration, and wound around catheter distal end 30. Catheter distal end 30 can be introduced the right atrium through, (i) the subclavian vein, requiring a catheter 28 length of about 30 to 40 cm, (ii) the internal jugular, requiring a catheter 28 length of about 30 to 40 cm or (iii) the femoral artery, requiring a catheter 28 length of about 110 cm.

Generally, cardiac ablation and mapping apparatus 12 can be a monopolar or bipolar treatment electrode system. It is capable of expanding so that membrane 14 becomes expanded within the heart chamber, and RF and thermal energy are delivered to the wall of the heart through membrane 14. RF and thermal energy are passed through the endocardium and subendocardium or deeper, for a time period sufficient to achieve a desired level of ablation at a arrhythmogenic foci.

In a monopolar mode, RF current flows through body tissue from a return electrode, in the form of a conductive pad applied to the patient's outer skin. Maximum heating occurs where the current density is the greatest.

Electric current flowing through the endocardium causes heating due to resistance of the tissue. Arrhythmogenic foci ablation can be accomplished as a relatively simple medical procedure.

For purposes of this disclosure, an insulator is a barrier to thermal or electrical energy flow. Membrane 14 conforms tightly with the interior of the heart so that substantially all of the heart wall is in contact with a conductive surface of membrane 14. Membrane 14 fits substantially into the entire heart chamber, and membrane 14 does not have to be moved about the heart to complete the treatment. Membrane 14 is made of a material that suitably conforms to a surface to be ablated, and can have a thickness in the range of about 0.01 to 2.0 cm. The electrolytic solution delivered to membrane 14 can be heated. Fluid flow can be continuous or non-continuous.

Referring now to FIG. 3, a plurality of treatment electrodes 34 are positioned on an exterior surface of membrane support 16. There is no direct energy delivery of RF or thermal energy from treatment electrodes 34 to the endocardium.

Figure 4:
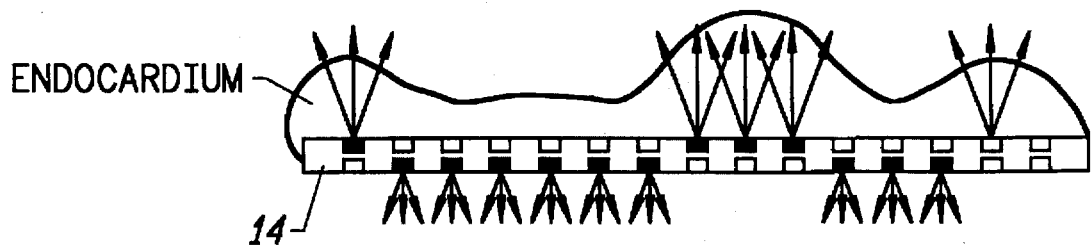
FIG. 4 is an illustration of n ablation device with direct ablation of the endocardium by treatment electrodes.
Figure 6:
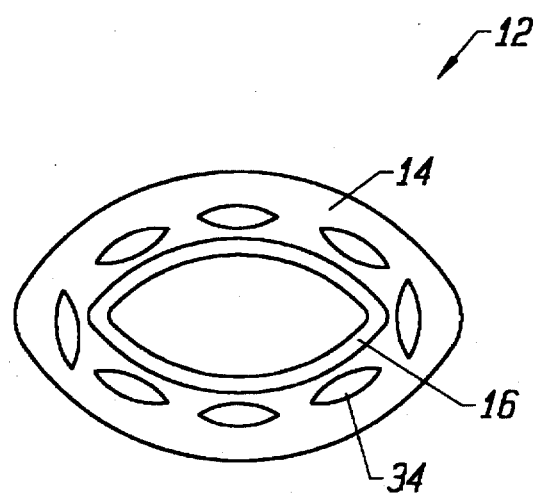
FIG. 6 is a cross-sectional view of the ablation and mapping apparatus of the invention with the treatment electrodes disposed within the membrane.
Figure 5:
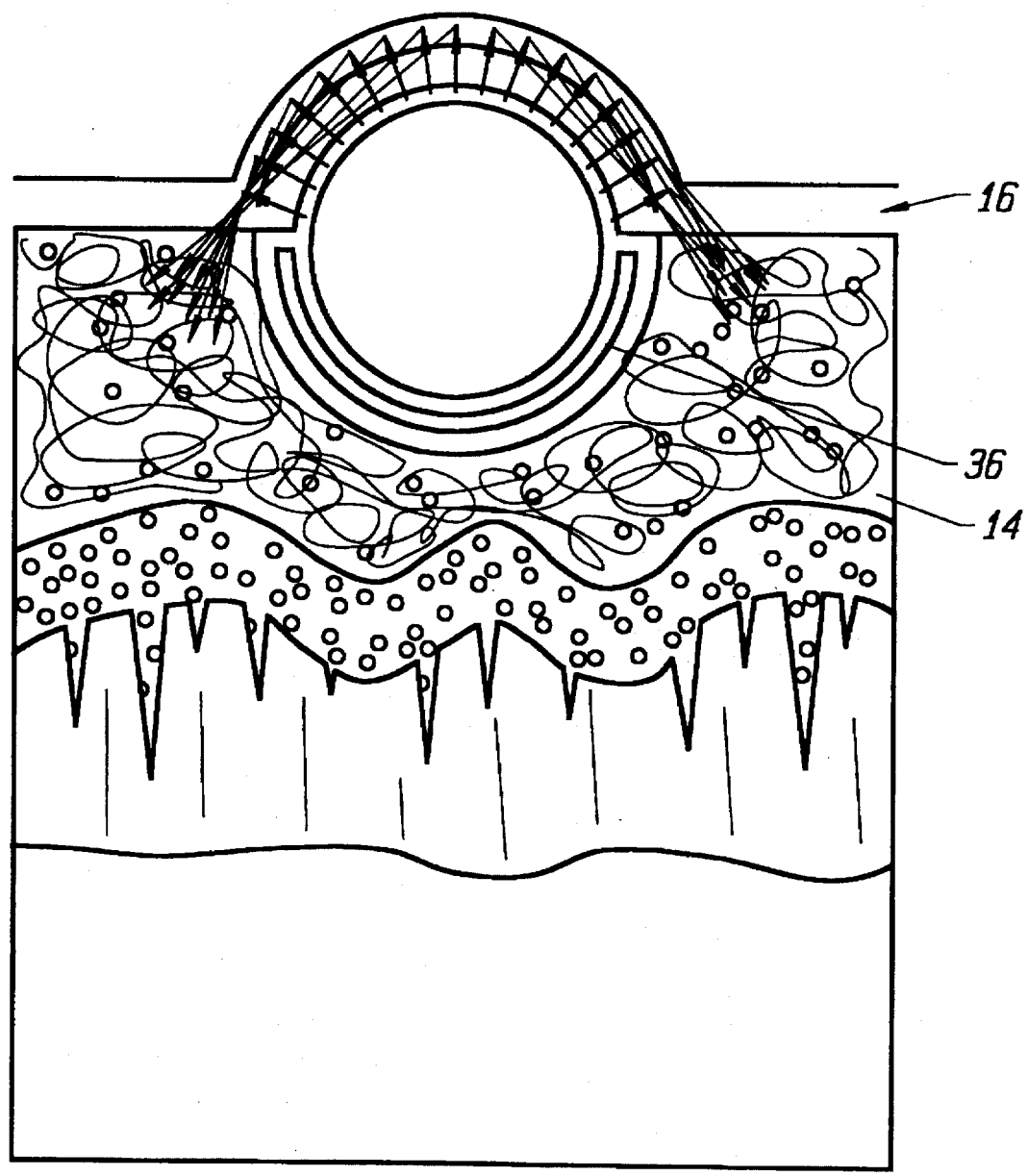
FIG. 5 is a sectional of the ablation apparatus of the invention with an insulator positioned on a side of an electrode that is adjacent to the membrane.

The results of having treatment electrodes 34 in direct contact with the endocardium are illustrated in FIG. 4. An uneven penetration of energy to the endocardium is produced. There is too much ablation for those ares of the endocardium adjacent to a treatment electrode. This problem is compounded as the number of treatment electrodes 34 adjacent to the endocardium is increased. Separation of treatment electrodes 34 from the endocardium reduces this effect. Additionally, the inclusion of an insulator 36, as shown in FIG. 5, prevents RF energy from treatment electrodes 34 to pass directly from treatment electrodes 34 through membrane 14. Instead, RF energy is applied indirectly to the endocardium, causing a thermal effect in the tissue. RF energy from treatment electrodes 34 arcs out through membrane 14. Membrane support 16 can serve as a second insulator. When treatment electrodes 34 are positioned in membrane 14, as shown in FIG. 6, then insulator 36 can still be used and positioned on a surface of a treatment electrode 34 that is in a facing relationship to the endocardium. Again, energy arcs through membrane 14, and there is no direct delivery of RF or thermal energy to the endocardium.

Figure 7:
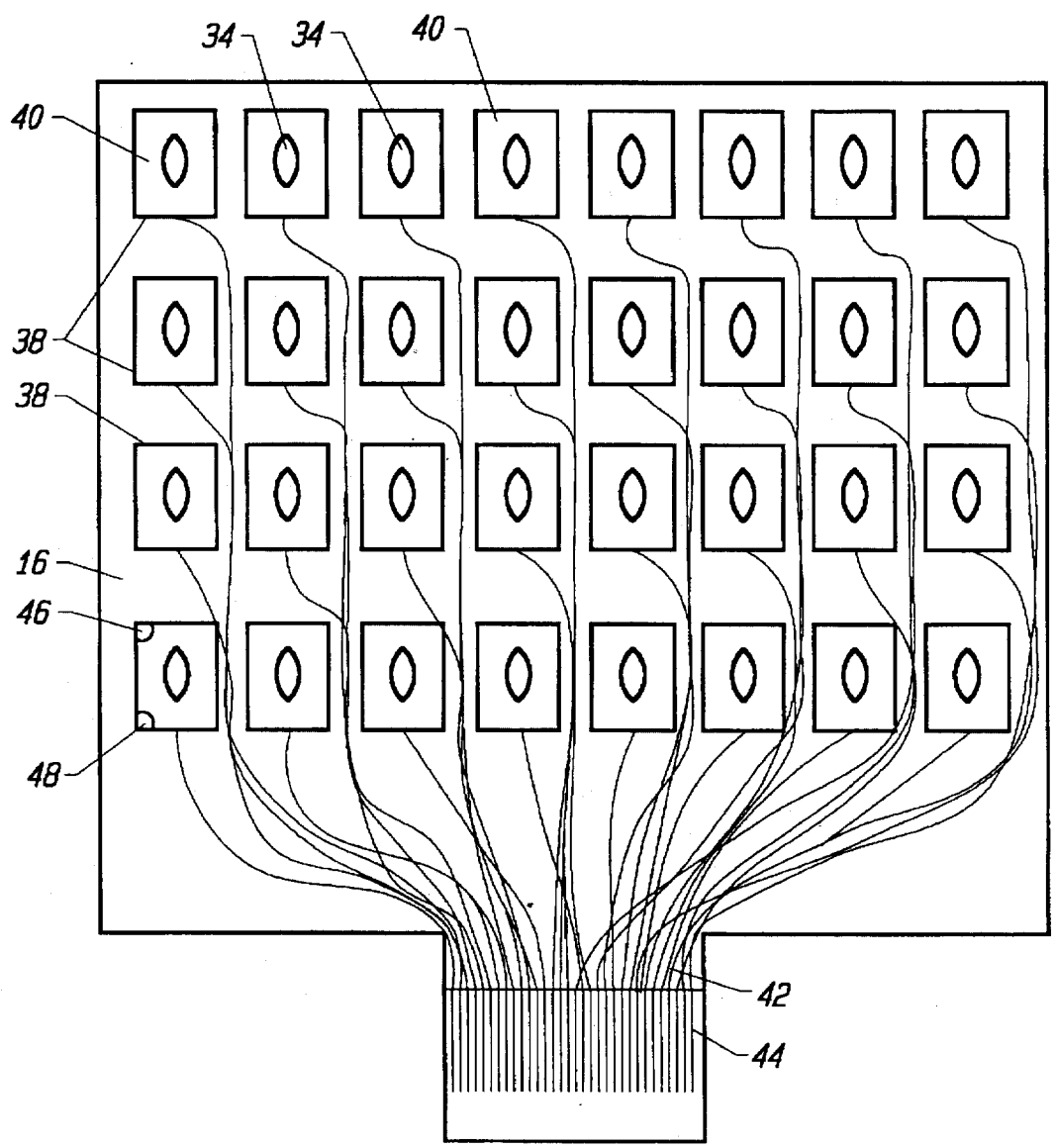
FIG. 7 is a perspective view of a circuit on the membrane support with treatment electrode segments.

Referring now to FIG. 7 a circuit 38, which can be flexible, and made of individual segments, can be a printed circuit that is deposited, etched or painted with a conductive ink on membrane support 16, or on a separate support member. Insulation 36 can be applied on the appropriate side of each segment 40 or treatment electrode 34 that faces membrane 14. Each segment 40 or treatment electrode 34 connects to a separate feedwire 42, with all of the wires going to a ribbon connector 44. Feedwires 42 are insulated. Each treatment electrode 34 or segment 40 is wired with a constant wire in order to receive RF energy from an RF energy source. A copper wire is connected to each constantan wire. This results in the formation of a T.type thermocouple "TC".

RF power is applied to the desired treatment electrode 34, delivering energy only to a selected site of the endocardium. In this way, treatment electrodes 34 and circuit 38 are multiplexed. The size of individual treatment electrodes 34 and segments 40 is designed to provide the correct current density. RF power can be sequentially supplied to each treatment electrode 34, to feedwire 42 in ribbon connector 44, or it can be applied to only certain selected feedwires 42, enabling only selected treatment electrodes 34 to deliver RF and thermal energy individually to the endocardium.

One or more impedance monitors 46 can be used to confirm, before an ablation event, that good coupling of energy is achieved. Also included is one or more thermal sensors 48. Thermal sensors 48 are conventional thermistors or thermocouples, and are positioned on treatment electrodes 34 or segments 40.

Figure 8:
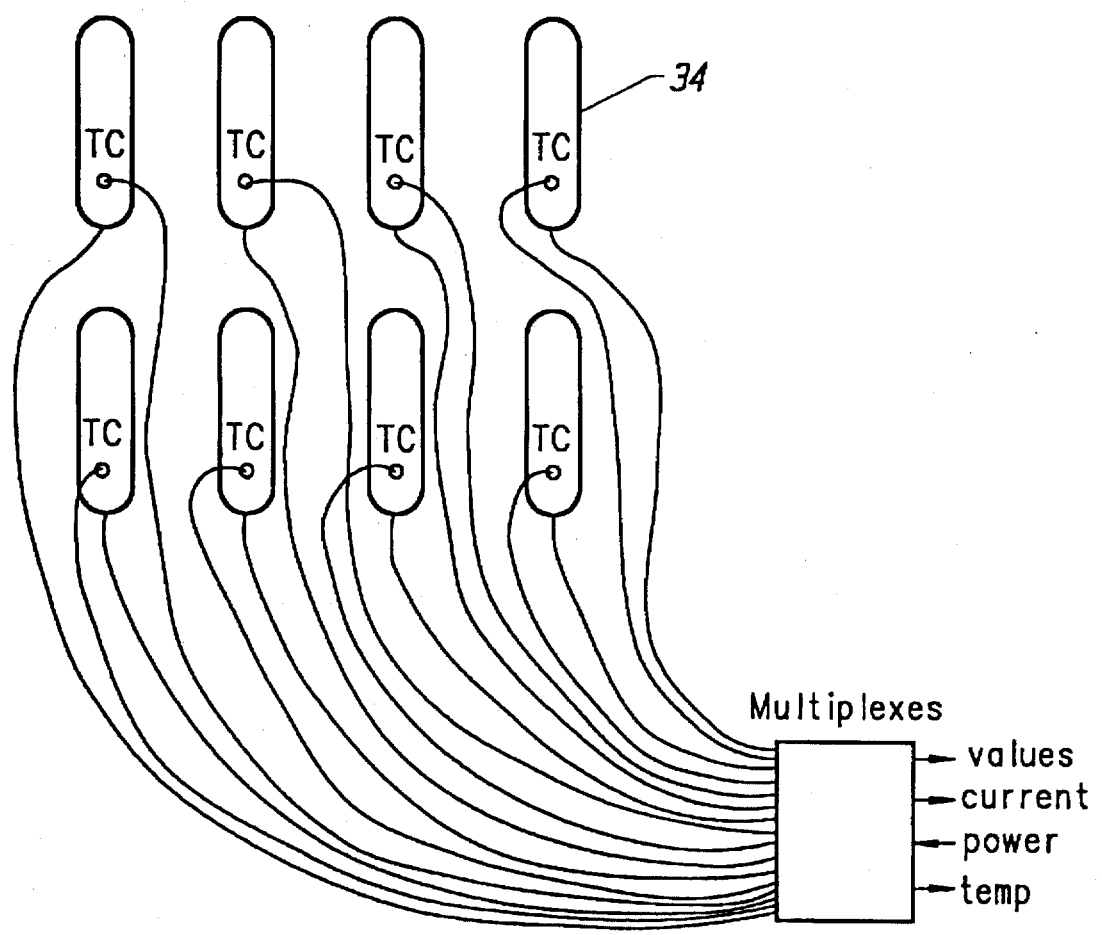
FIG. 8 is an illustration of a plurality of treatment electrodes that are suitable for use with the present invention.

With reference now to FIG. 8, individual treatment electrodes 34 can be used and multiplexed in either of monopolar or bi-polar schemes. Segments 40 and treatment electrodes 34 are capable of multiplexing so that only one delivers RF energy at a particular time period. RF energy is selectively delivered, in that the amount of energy delivered by each segment 40 or treatment electrode 34 can vary, depending on the detected characteristics of endocardium at a particular area.

Figure 9:
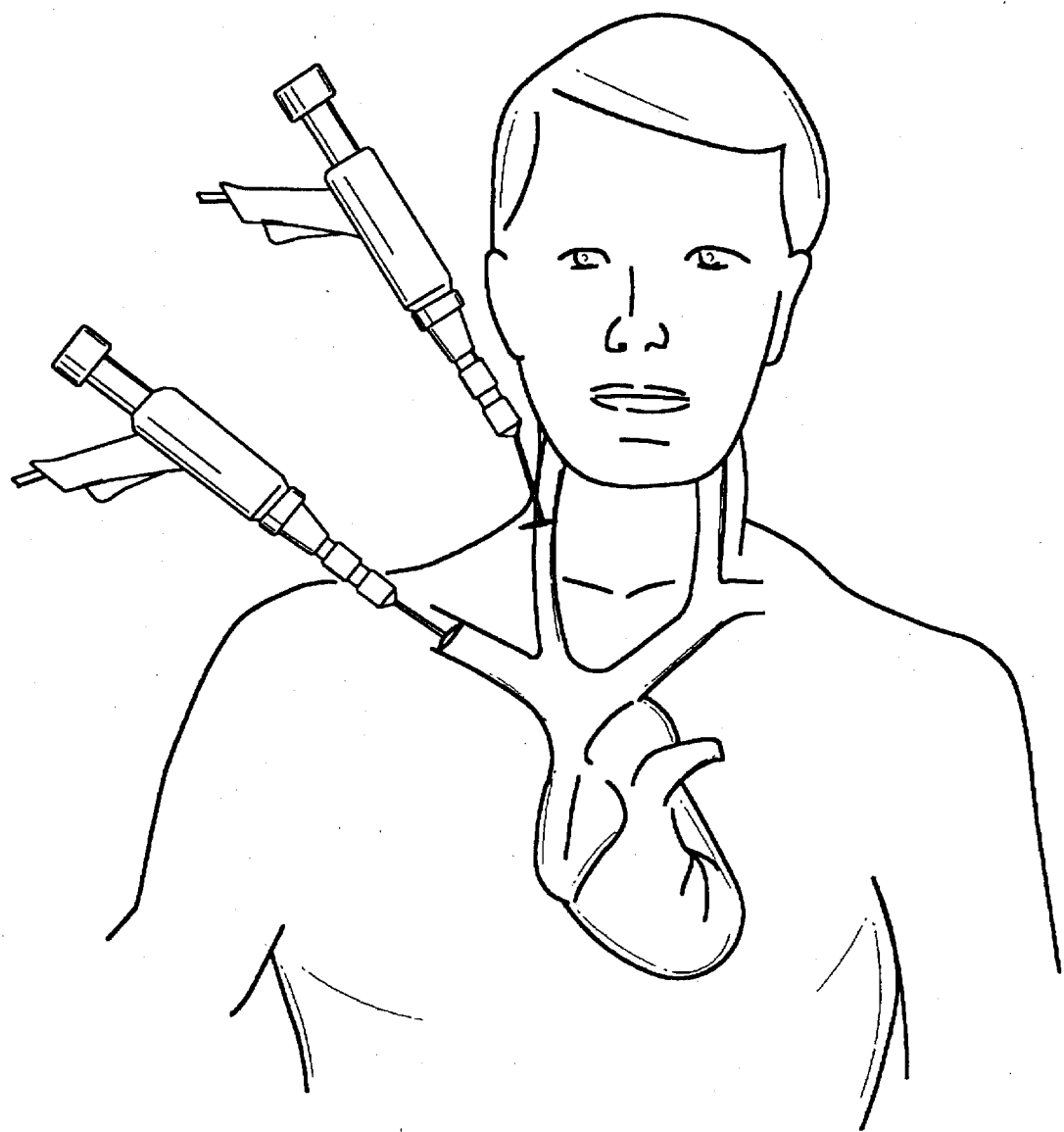
FIG. 9 illustrates the introduction of the ablation apparatus into the desired vein.
Figure 10:
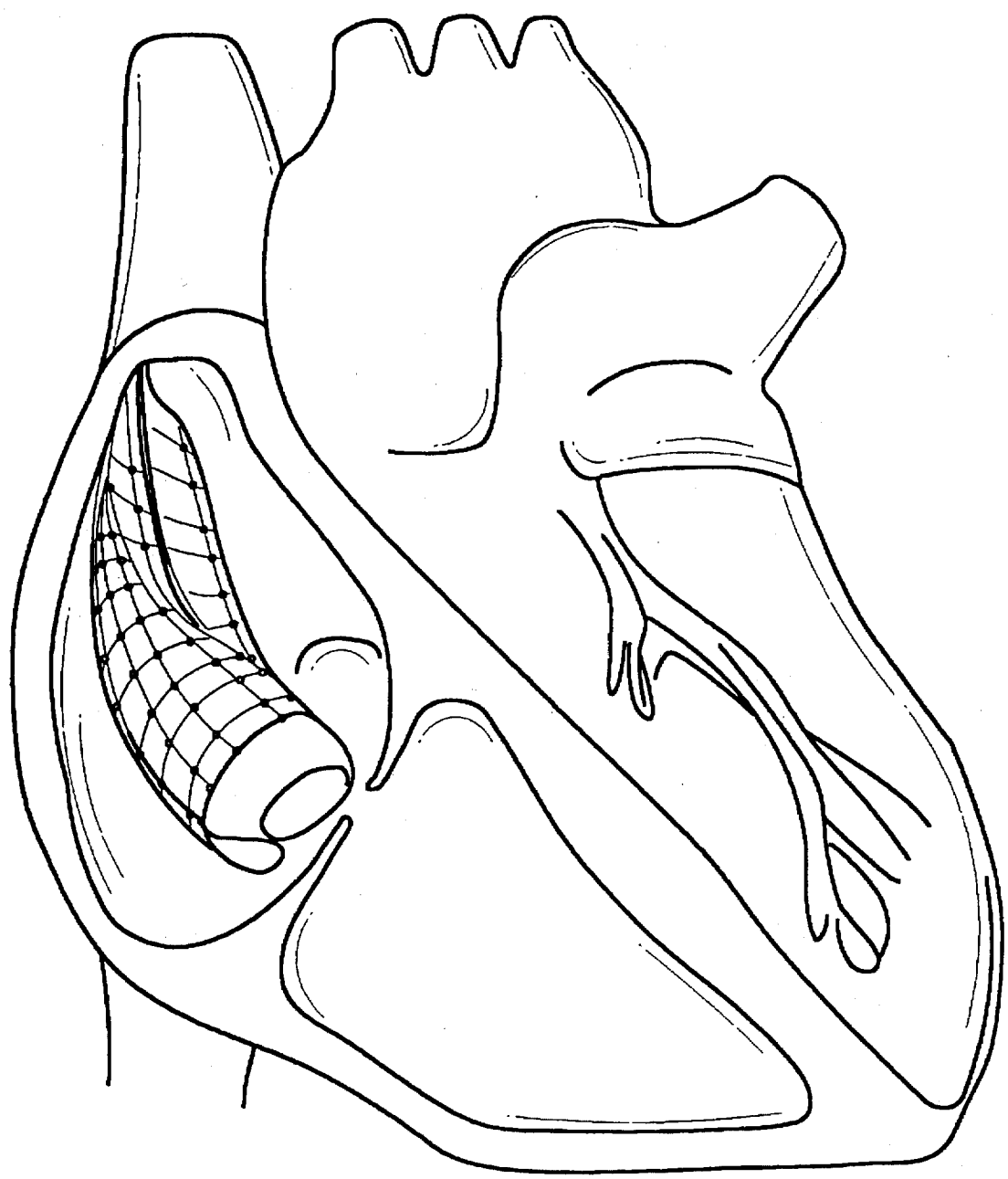
FIG. 10 is a cross-sectional view of the ablation apparatus being positioned in the right atrium before it is expanded.
Figure 11:
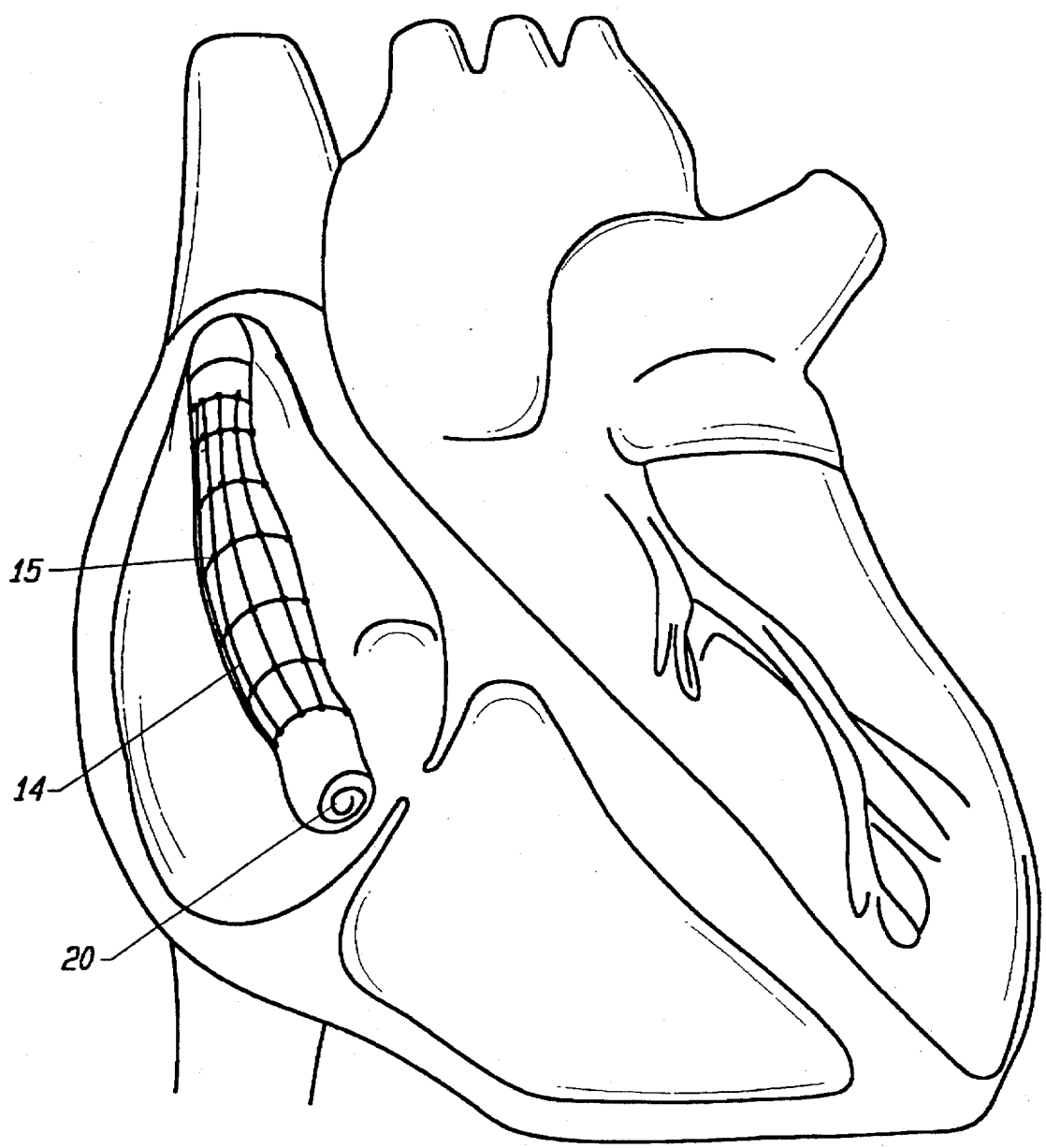
FIG. 11 is a cross-sectional view of the ablation apparatus being positioned in the right atrium, showing one end of the ablation apparatus that will become seated in the atrium.
Figure 12:
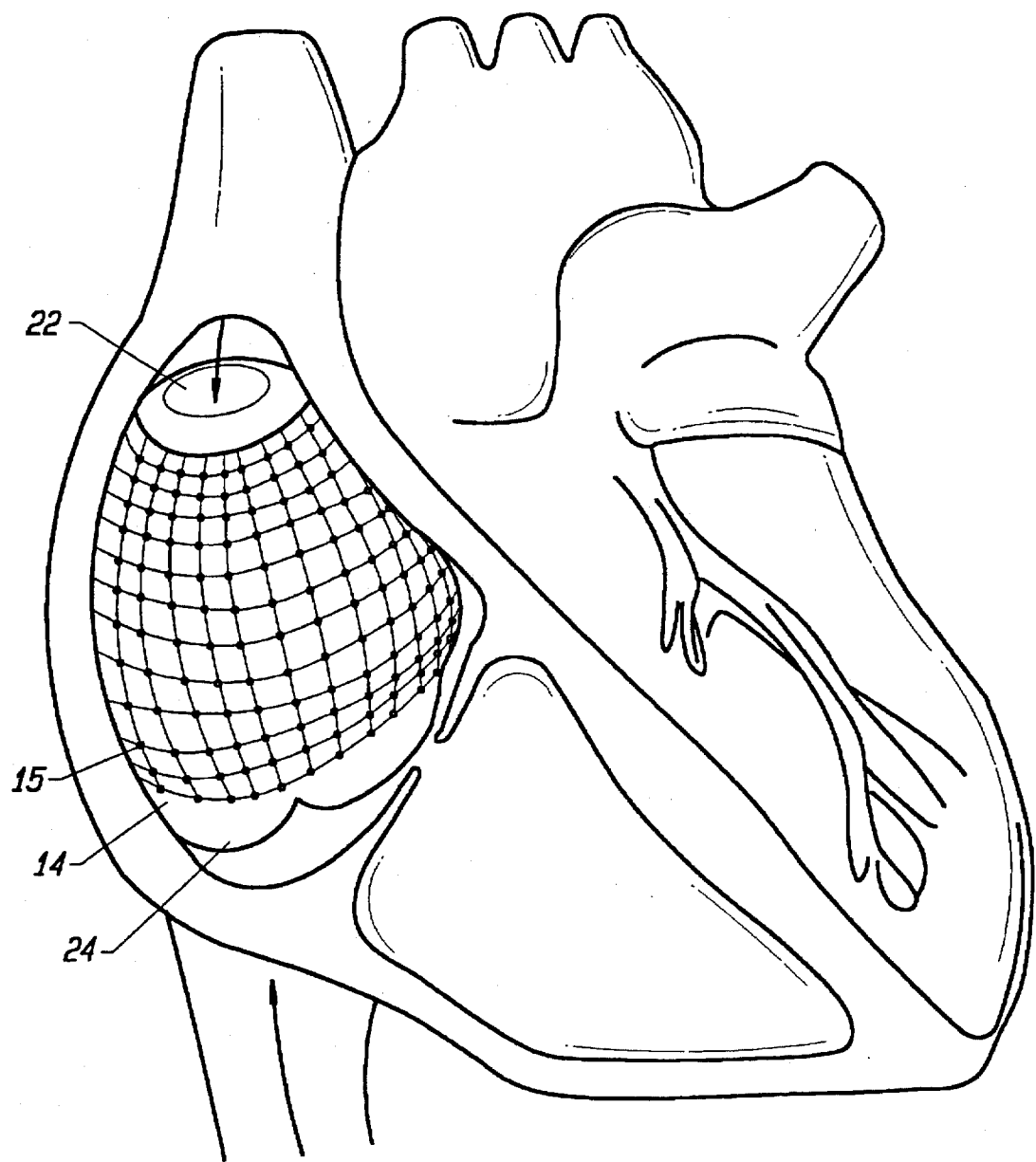
FIG. 12 illustrates an expanded ablation apparatus positioned in the right atrium.

In FIG. 9, ablation apparatus 12 is shown as being introduced through the jugular or subclavian veins. In FIG. 10, ablation MAP electrodes 15 are shown as being positioned on an exterior surface of membrane 14 in a folded or rolled configuration as ablation apparatus 12 is introduced into the right atrium. Ablation apparatus 12 begins to unfold in FIG. 11 with end 20 seeking to be positioned in the tricuspid annulus. In FIG. 12, ablation apparatus 12 has become expanded so that membrane 14, with MAP electrodes 15, is in a contacting relationship with the wall of the right atrium. Blood flow is not impeded and flows through lumen 26 of membrane support 16 through apertures 22 and 24 respectively. With ablation apparatus 12 in its expanded state and positioned in an atrium, there is constrained contraction of the atrium. Mapping and analysis of the heart chamber activation, with the use of MAP electrodes 15, occurs substantially at once and can occur within less than ten heart beats or sufficiently long enough to obtain the required intracavity map.

Figure 13:
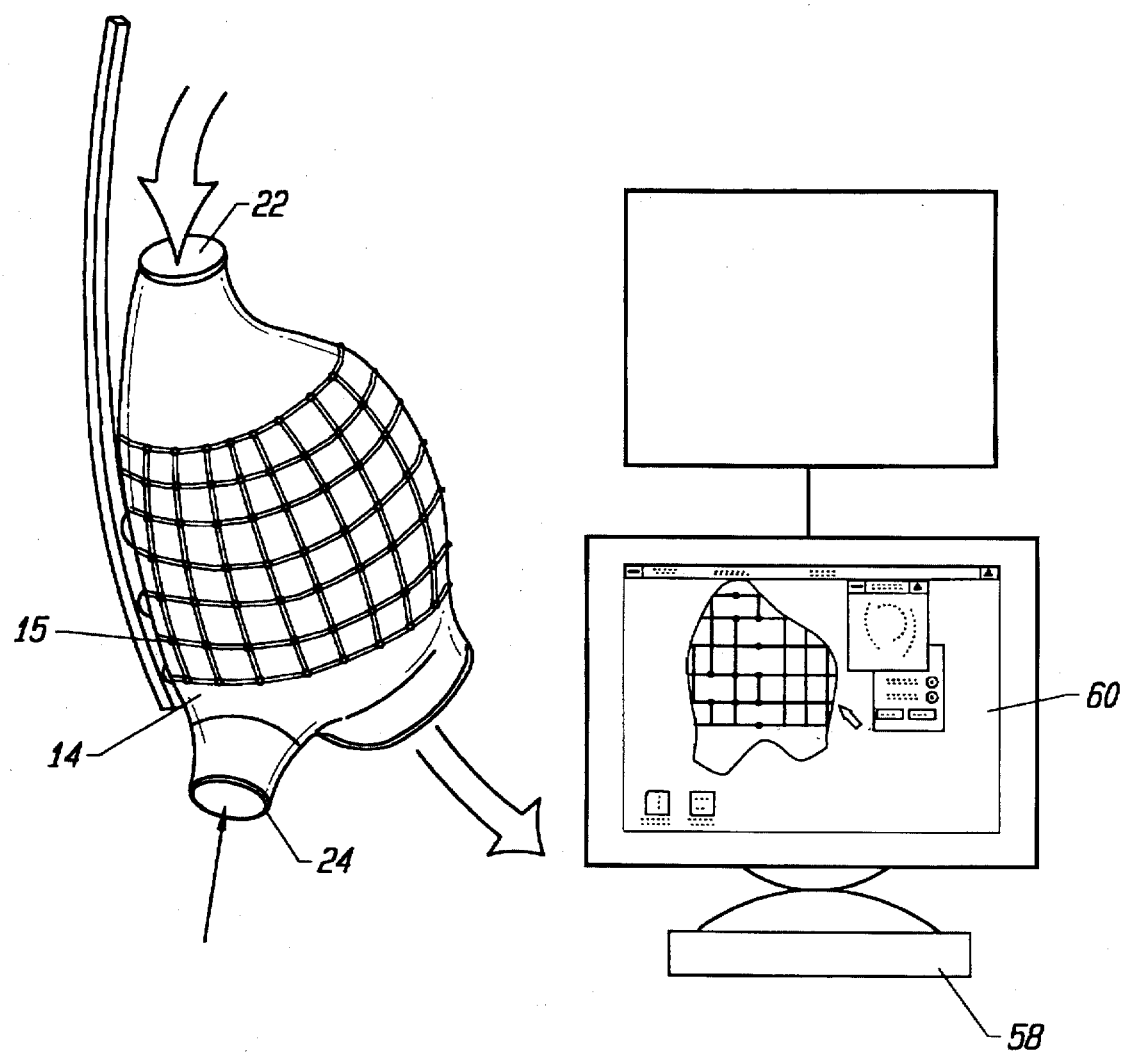
FIG. 13 illustrates the output from the ablation apparatus on a display screen.

Passive blood flow through the superior vena cava, inferior vena cava and the tricuspid value is shown in FIG. 13. The electrical data output and intracavity map can be presented on a viewing screen.

Figure 14:
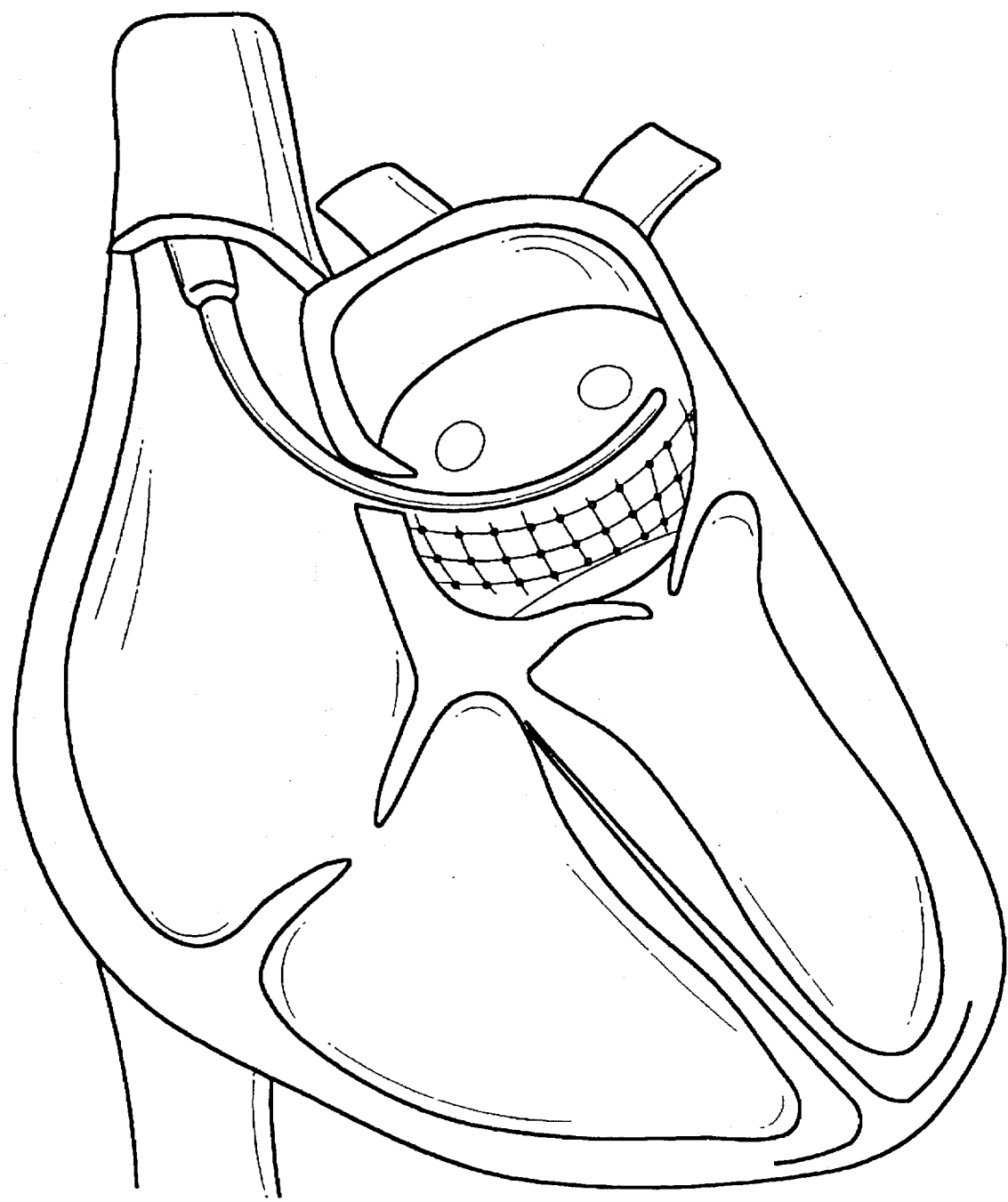
FIG. 14 illustrates placement of the ablation apparatus in the left atrium.

In FIG. 14, ablation apparatus 12 is introduced into the left atrium. There are four pulmonary veins. Ablation apparatus 12 covers only two of the pulmonary veins at one time and the mitral valve. Therefore, ablation apparatus 12 is flipped over in the right atrium to cover the other two pulmonary veins and mitral valve. Ablation apparatus 12 is introduced into the left atrium either with a stick type of structure across the septal wall, or through the patent ductus.

Figure 15:
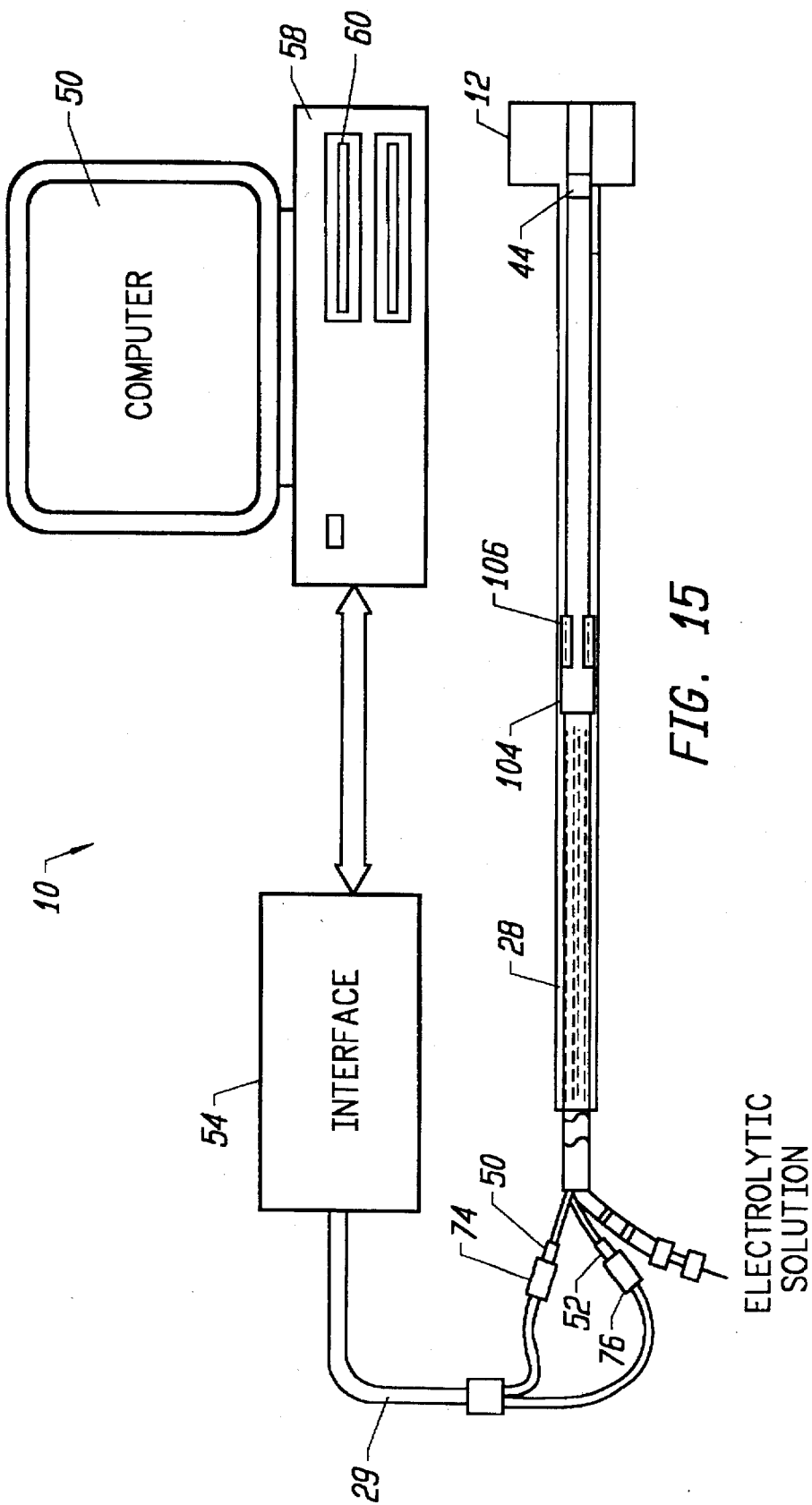
FIG. 15 is a schematic diagram of the cardiac ablation and mapping system of the invention.

Referring now to FIG. 15, endocardial ablation and mapping system 10 is illustrated. A high voltage connector 50 and a signal connector 22 are connected the electrodes (not shown) and form part of catheter 28. A cable 29 is connected to an interface module 54 which supplies and receives signals to and from the electrodes, and from a computer 58 that is provided with a disc drive 60 and a monitor 62. It is also provided with a keyboard (not shown) for use in controlling the operation of computer 58.

Figure 16:
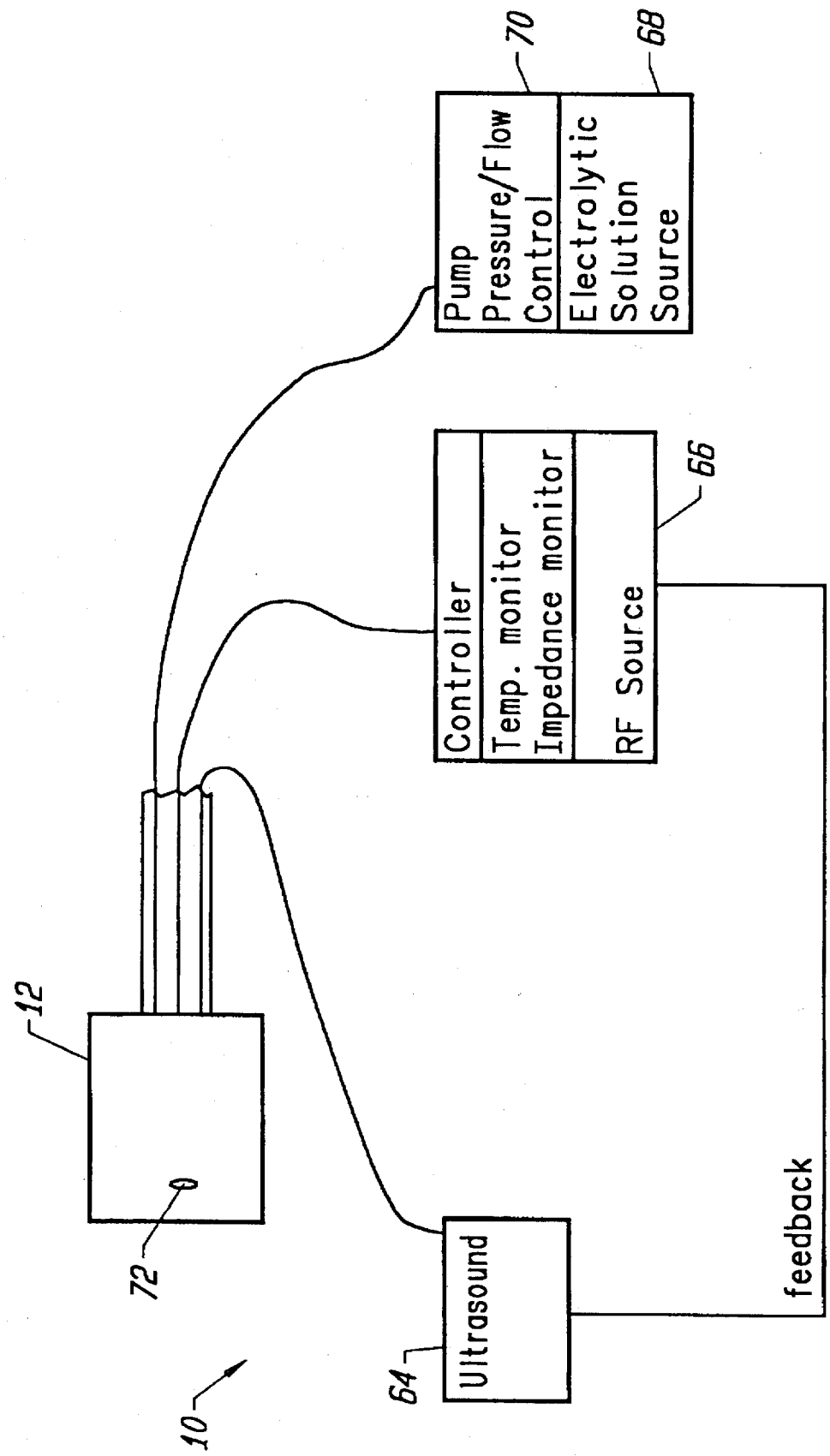
FIG. 16 is a block diagram of the cardiac ablation and mapping system of the invention.

As shown in FIG. 16, ablation system 10 can include an ultrasound source 64, RF energy source 66 and an electrolytic solution source 68, all coupled to ablation apparatus 12. RF energy source 66 can incorporate a controller, as well as both temperature and impedance monitoring devices.

Electrolytic solution source 68 can include a pump/pressure flow control device 70, well known to those skilled in the art. A heating device for heating the electrolytic solution can be associated with electrolytic solution source 68. Suitable heating devices include but are not limited to coils, bipolar treatment electrodes, catalysts, and other devices. Ultrasound energy source 64 is coupled to one or more ultrasound transducers 72 that are positioned in or on membrane 14. An output is associated with ultrasound source 64 and RF energy source 66.

Each ultrasound transducer 72 can include a piezoelectric crystal mounted on a backing material. An ultrasound lens, fabricated on an electrically insulating material, is mounted between the piezoelectric crystal and membrane 14. The piezoelectric crystal is connected by electrical leads to ultrasound source 64. Each ultrasound transducer 72 transmits ultrasound energy through membrane 14 and into adjacent endocardial tissue. Ultrasound transducers 72 can be in the form of an imaging probe such as Model 21362, manufactured and sold by Hewlett Packard Company, Palo Alto, Calif.

Electrical resources acquire electrical data from the heart and provide electrical function feedback to RF generator 66. RF generator 66 then supplies a therapeutic output to electrodes 34. These electrical resources map the heart with MAP electrodes 15 to acquire activation data, seek the origin of the arrhythmia, provide early local endocardium activation, provide ablation, further mapping, and further ablation if required.

Operation and use of cardiac ablation and mapping apparatus 12 in connection with interrace module 56, and computer 58 is now described.

As soon as the distal end 30 of catheter 28 is positioned within the desired chamber, high voltage connector 50 and signal connector 52 are interconnected with mating connectors 74 and 76, (FIG. 15) so that the plurality of electrodes are connected to interface module 54 and computer 58. Membrane 14 is then expanded by electrolytic solution, causing membrane 14 to become distended and be self-retained in the heart.

Electrolytic solution in membrane 14 can be heated to a pre-selected temperature, which can be modified and adjusted as necessary. For example, electrolytic solution can be heated and maintained at a temperature between about 60 to 90 degrees C. By providing a heated electrolytic solution, there is a reduction in the amount of time needed to complete a satisfactory ablation of arrhythmogenic foci.

Once this is accomplished, membrane 14 is in a contacting, conforming relationship to the wall of the chamber of the heart. When membrane 14 becomes expanded, its conductive surface and MAP electrodes 15 are in a contacting relationship with the wall of the chamber. It moves with the chamber with its constrained contraction and expansion. Lumen 26 in membrane support 16 permits blood to flow in and out of the heart chamber.

Figure 17:
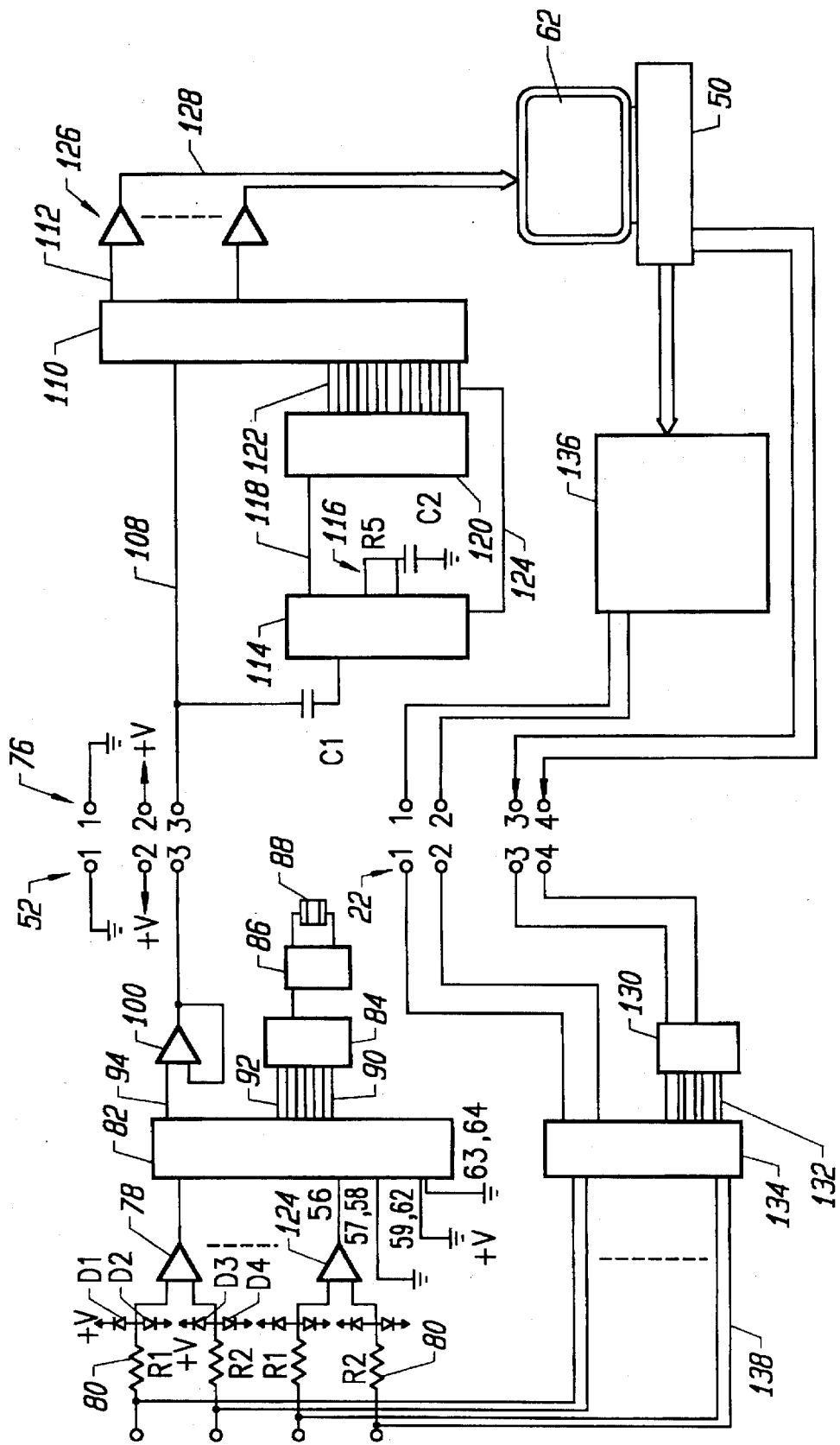
FIG. 17 is a circuit diagram of the cardiac ablation and mapping system of the invention.

In one embodiment, shown in FIG. 17, the plurality of treatment electrodes 34 can be operated in the bipolar mode. Bipolar treatment electrode pairs are connected to a differential amplifier 78. Each of the differential amplifiers 78 is provided with input circuitry 78 which consists of current limiting resistors R1 and R2 connected to diodes D1 and D2, on opposite sides of the input line, with the diode D2 being connected to ground and diode D1 being connected to a positive voltage. Diodes D4 and D6 are connected to the other input line with diode D4 being connected to ground and diode D6 being connected to the positive voltage.

These serially connected diodes serve to protect the inputs to differential amplifiers 78 during the time that ablation voltages are being applied.

The input circuitry has the capability of limiting the voltage rise at the inputs of differential amplifiers 78 to approximately ½ volt. Differential amplifiers 78 have a suitable gain as for example typically between 100 and 500. Since the endocardial signals that are received from the heart are of relatively high amplitude, a very high gain is not required from differential amplifiers 78.

Outputs of differential amplifiers 78 are connected by a number of lines, depending of the number of treatment electrodes and pairs, to an analog multiplexer 82. Multiplexer 82 can have a number of inputs, as for example, 64. Inputs are connected to expandable member 16 at connector 44. Certain inputs can be grounded. Other inputs can be connected to a positive voltage supply and other inputs connected to ground. One or two of the inputs can be utilized for providing a synchronization signal for demultiplexing, as hereinafter described.

Multiplexer 82 is driven by a 6 bit binary counter 84 which is supplied with a clock frequency from an oscillator 86 that is controlled by crystal 88 of a suitable frequency as for example, 200 KHz. The 200 KHz oscillator frequency provides a five microsecond cycle length per channel as shown in waveform 96 of FIG. 18. Counter 84 supplies an output 90 on six lines 92 to multiplexer 82. Multiplexer 82 is provided with an output line 94 which is controlled by binary counter 84 so that the output from each of the amplifiers 78 appears on output line 94 for the five microsecond pulse length provided by oscillator 86.

Figure 18:
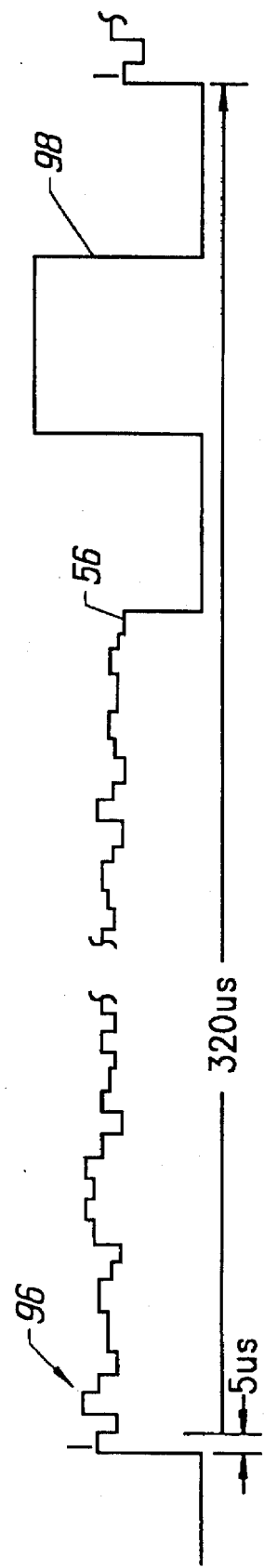
FIG. 18 is a timing diagram for the circuitry shown in FIG. 17.

In FIG. 18, waveform 96 shows information being received on 56 channels with each channel having a 5 microsecond duration, followed by a synchronizing pulse 98 that is 20 microseconds wide; to complete one cycle of multiplexer 82 of 320 microseconds; followed by the next 320 microsecond cycle. This provides an effective sampling rate of about 3000 samples per second.

Referring again to FIG. 17, output 94 is connected to a buffer amplifier 100 which provides its output 102 on pin 3 of connector 52. The other pins 1 and 2 in connector 52 are connected to ground and a plus voltage respectively in interface module 54.

A multiplexer chip 104 is connected to leads 106 which in turn are connected to selected treatment electrodes 34 (FIG. 15). The power of multiplexer chip 104, associated with cardiac ablation and mapping apparatus 12, is supplied from interface module 54 through pins 1 and 2 of connector 76, as shown in FIG. 17. Pin 3 of connector 76 receives the output signal from pin 3 of connector 52, and supplies it through a line 108 to a demultiplexer 110. Demultiplexer 110 is supplied with a plurality of output channels 112. Assuming there are 64 input channels in multiplexer 82, there will be a corresponding number of output channels 112 in demultiplexer 110.

The information on line 108, containing the synchronizing signal, is also supplied through a capacitor C1 to a phase locked loop 114, and is connected to an RF filter network 116 consisting of a resistor R5 and a capacitor C2 connected to ground. Phase locked loop 114 is provided with an output line 118 and has provided thereon a reconstructed 200 KHz voltage controlled oscillator output which is supplied to a counter 120. Counter 120 is provided with a plurality of output lines 122 which are connected to demultiplexer 110. Lines 122 are provided with frequencies ranging from 100 KHz to 3,125 KHz, with the 3,125 being connected to phase locked loop 114 by a line 124 which serves to couple the VCO output to phase locked loop 114. The use of the phase locked loop 114 allows the reconstruction of the 200 KHz clock, which is synchronized to the 200 KHz in multiplexer chip 104.

Demultiplexer 110 serves to demultiplex the information supplied from multiplexer 82 and supplies it on the 56 channels 112 to circuitry 126; which includes sample and hold circuitry, filter circuitry and A/D converters, to provide an output on lines 128 in the form of a signal which is supplied to computer 58 and display monitor 62. Computer 58 is provided with software that has the capability of analyzing information being supplied to it by utilizing sampling techniques well known to those in the art. Computer 58 performs an analysis of the information including but not limited to mapping of the heart to acquire electrical activation data and early endocardial activation. The use of propagation and delay time analysis computer 58 identifies and isolates the area within a heart chamber which may contain an arrhythmogenic foci to be ablated. This information is displayed on the screen of monitor 62 so that it can be reviewed by the physician who then decides whether or not ablation is desirable.

Referring again to FIGS. 15 and 17, let it be assumed that arrhythmogenic foci have been located, and it is desired to ablate the arrhythmogenic foci. After the mapping has been accomplished by use of cardiac ablation and mapping apparatus 12 (MAP electrodes 15), the same cardiac ablation and mapping apparatus 12, while still in place in the heart chamber, is used for accomplishing the ablation with treatment electrodes 34. The attending physician inputs the desired commands to the keyboard connected to computer 58 to give the command to proceed with an ablation. As soon as such a command is received by computer 58, it sends a channel number serially to pin 3 of connector 74; which is connected to the corresponding pin 3 of connector 50 in a serial to parallel shift register 130 that is disposed in electrode ablation apparatus 12. Shift register 130 supplies the channel number to demultiplexer 110 on the six lines 132 to a high voltage demultiplexer 134. Shift register 130 is provided with a clocking signal on pin 4 of connector 50 that is supplied with a clock signal on the corresponding pin 4 of connector 74 from computer 58.

The output of computer 58 is also connected to a high voltage ablation power supply 136. High voltage ablation power supply 136 is programmable as to channel number and the amount of energy to be supplied on the channel. High voltage ablation power supply 136 supplies its output to pins 1 and 2 of connector 74, connected to corresponding pins 1 and 2 of connector 50, which are connected to demultiplexer 134. Demultiplexer 134 is provided with high voltage transistors which can tolerate the ablation voltages supplied by ablation power supply 136. Upon command, ablation power supply 136 supplies a high voltage, high frequency (typically 50–100 volts at 750 KHz to 1 MHz) pulse across the pins 1 and 2 of connector 74. This high voltage pulse appears on the corresponding the pins 1 and 2 of connector 50, and is supplied by demultiplexer 134 to the appropriate channel and appropriate treatment electrode pair through lines 138 connected to leads 106. This pulse appears across treatment electrode pair 34 and causes an ablation to occur in the endocardium of right atrium between treatment electrode pair 34. Alternatively, ablation can be accomplished between one of the treatment electrode pairs 34 and an external ground treatment electrode placed on the chest of the patient. In this manner, it can be seen that a highly controlled ablation is provided which is precisely positioned with respect to the selected treatment electrode pair 34.

Several milliseconds after the ablation pulse has been supplied to the appropriate electrode pair of treatment electrodes 34, mapping can again be resumed to ascertain whether or not arrhythmogenic foci are still present. If the mapping indicates that at least a portion of the re-entry pathway is still present, high voltage pulses can be programmed by computer 58 and supplied to other appropriate treatment electrode pairs 34 until the re-entry pathway has been destroyed.

Programmed stimulation can be performed by using a selectable number of MAP electrodes 15. In this mode of operation, interface 54 provides a programmable level of low voltage pulses (5–10 volts) via the high voltage connector 58 to stimulate the heart with synchronized pulses in order to induce or convert an arrhythmia.

Staggered radiopaque markers can be utilized to ascertain which segments 40 are located closest to the anatomical point of interest in the heart cavity, as for example, the right atrium. By observing this staggered relationship of the markers, the physician can select the signals coming from a specific segment 40 to analyze the same in computer 58.

It is possible to measure the pressure in the right atrium during mapping or ablation. By measuring the pressure in the right atrium, it is possible to ascertain when the right atrium is filled with blood, or whether it is being squeezed. The timing of the ablation can be such that ablation occurs when the right atrium is squeezed to its smallest size. This may be desirable because at this point there will be the best contact, though membrane 14 between segments 40 or treatment electrodes 34 and the heart wall forming the right atrium. In addition, it is desirable to carry out the ablation at this point in time because the amount of blood in the right atrium is at a minimum. Thus, more of the energy created by the ablation pulse is dissipated into the heart wall rather than into the pool of blood in the right atrium. Also, in order to accomplish this, a pressure transducer 188 can be provided in cardiac ablation and mapping apparatus 12, and connected to electrical wires (not shown) into multiplexer 82.

Cardiac ablation and mapping apparatus 12 can be provided with an increased number or decreased number of treatment electrodes 34 if desired. Additional channels can be readily provided in multiplexer 82 and demultiplexer 110. The shape of segments 40 can be made so that they conform to the wall of the heart, through membrane 14, as it expands and contracts through the entire cardiac cycle. Segments 40 do not directly touch the wall of the heart chamber. Instead, they are preferably formed on membrane support 16. Membrane 14 maintains intimate contact with the wall of the heart chamber, minimizing the amount of energy which is dissipated into the blood pool within the cavity of the heart during ablation.

Once the desired procedures are completed, cardiac ablation and mapping apparatus 12 is removed from the heart chamber.

The following examples illustrate the ablation affect of ablation system 10. In each example, ablation system 10 was used to ablate four quadrants (Q1 through Q4) of a tissue site. It was determined that substantially even ablation was achieved at each quadrant, even with different RF energies, establishing that ablation system 10 provides selectable control of tissue ablation.

| Size | L - mm | W - mm | Depth - mm | Average Power Delivered |
|------|--------|--------|------------|-------------------------|
| Settings | Time - min: 7.0 | Power - Watts: 9.5 | | |
| Example 1 | | | | |
| Q1 | 14.43 | 11.39 | 3.22 | 9.11 Watts |
| Q2 | 13.90 | 11.26 | 3.83 | |
| Q3 | 14.34 | 12.75 | 3.43 | |
| Q4 | 16.87 | 11.60 | 3.55 | |
| Example 2 | | | | |
| Q1 | 14.89 | 13.60 | 3.26 | 9.13 Watts |
| Q2 | 15.70 | 12.68 | 3.85 | |
| Q3 | 16.10 | 12.79 | 3.10 | |
| Q4 | 16.90 | 13.58 | 3.78 | |

-continued

| Size | L - mm | W - mm | Depth - mm | Average Power Delivered |
|---|---|---|---|---|
| Example 3 | | | | |
| Q1 | 15.67 | 12.41 | 3.24 | 9.09 Watts |
| Q2 | 12.60 | 11.24 | 3.19 | |
| Q3 | 13.85 | 12.49 | 3.42 | |
| Q4 | 14.87 | 10.82 | 3.37 | |
| Example 4 | | | | |
| Q1 | 15.36 | 11.54 | 3.37 | 9.06 Watts |
| Q2 | 15.12 | 10.78 | 3.18 | |
| Q3 | 15.69 | 10.86 | 3.22 | |
| Q4 | 15.27 | 11.15 | 3.38 | |
| Settings | Time - min.: 7.0 | Power - Watts: 9.0 | | |
| Example 5 | | | | |
| Q1 | 15.04 | 10.63 | 2.71 | 8.58 Watts |
| Q2 | 14.36 | 10.18 | 3.19 | |
| Q3 | 14.68 | 11.70 | 2.78 | |
| Q4 | 15.68 | 11.61 | 3.03 | |
| Example 6 | | | | |
| Q1 | 14.78 | 11.90 | 2.78 | 8.55 Watts |
| Q2 | 14.06 | 10.67 | 2.91 | |
| Q3 | 14.72 | 11.46 | 2.96 | |
| Q4 | 15.08 | 12.91 | 2.64 | |
| Example 7 | | | | |
| Q1 | 14.77 | 13.62 | 2.69 | 8.60 Watts |
| Q2 | 13.64 | 12.78 | 2.74 | |
| Q3 | 14.22 | 13.31 | 2.63 | |
| Q4 | 14.42 | 13.27 | 2.92 | |
| Example 8 | | | | |
| Q1 | 14.69 | 14.14 | 3.06 | 8.56 Watts |
| Q2 | 15.76 | 12.39 | 2.96 | |
| Q3 | 15.16 | 12.65 | 2.93 | |
| Q4 | 14.96 | 11.90 | 2.56 | |
| Settings | Time - min.: 7.0 | Power - Watts: 8.5 | | |
| Example 9 | | | | |
| Q1 | 15.02 | 11.98 | 2.17 | 8.20 Watts |
| Q2 | 15.11 | 12.71 | 2.20 | |
| Q3 | 15.69 | 13.12 | 2.24 | |
| Q4 | 16.18 | 12.73 | 2.14 | |
| Example 10 | | | | |
| Q1 | 14.91 | 13.04 | 2.29 | 8.23 Watts |
| Q2 | 14.70 | 13.49 | 2.08 | |
| Q3 | 15.78 | 12.61 | 2.16 | |
| Q4 | 15.84 | 12.48 | 2.21 | |
| Example 11 | | | | |
| Q1 | 15.51 | 14.40 | 2.28 | 8.6 Watts |
| Q2 | 14.68 | 12.46 | 2.04 | |
| Q3 | 15.77 | 15.32 | 2.11 | |
| Q4 | 15.45 | 12.79 | 1.98 | |
| Example 12 | | | | |
| Q1 | 15.47 | 13.35 | 2.16 | 8.18 Watts |
| Q2 | 15.40 | 13.12 | 2.19 | |
| Q3 | 13.45 | 15.24 | 2.09 | |
| Q4 | 15.73 | 13.39 | 2.21 | |

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A cardiac ablation device for ablating tissue within a chamber of the heart comprising:
    a plurality of RF electrodes;
    a fluid permeable expandable member surrounding the electrodes;
    an electrical connector device connecting the electrodes to an RF energy source; and
    a source adapted to provide an electrolytic fluid to the expandable member to expand the expandable member to conform to at least a portion of the heart chamber and to cause said fluid to create a conductive path between the electrodes and an inner surface of the heart chamber.

2. The ablation apparatus of claim 1, wherein the member further comprises:
    electrical resources for acquiring electrical data from the heart and providing electrical function feedback to the RF power source which then supplies a therapeutic output to selected treatment electrodes of the plurality.

3. The ablation apparatus of claim 2, wherein the electrical resources includes devices for supplying a predetermined voltage at a predetermined frequency to selected treatment electrodes to cause ablation in a preselected location in the wall of the heart chamber.

4. The ablation apparatus of claim 1, wherein the treatment electrodes are multiplexed.

5. The ablation apparatus of claim 1, wherein the membrane is secured to a distal end of a catheter for insertion into and removal from the heart chamber.

6. The ablation apparatus of claim 1, wherein the membrane includes a deposition of ions to improve RF and thermal energy conductivity.

7. The ablation apparatus of claim 1, wherein the plurality of treatment electrodes are positioned in a spaced apart relationship within the member.

8. An endocardial ablation apparatus for introduction into a heart chamber formed by a wall, comprising:
    an expandable, flexible, fluid permeable member adapted to receive an electrolytic solution and become expanded to substantially conform a surface of the member to a surface within a heart chamber;
    a catheter for introducing the member into a heart chamber in a non-expanded state;
    means for delivering an electrolytic solution to the member to expand the member;
    a plurality of treatment electrodes covered by the member;
    an RF power source coupled to the treatment electrodes; and
    a source of electrolytic solution fluidly coupled to the member and for coupling the RF energy to the heart chamber.

9. The ablation apparatus of claim 8, wherein the member further comprises:
    electrical resources for acquiring electrical data from the heart and providing electrical function feedback to the RF power source which then supplies a therapeutic output to selected treatment electrodes of the plurality.

10. The ablation apparatus of claim 9, wherein the electrical resources includes devices for supplying a predetermined voltage at a predetermined frequency to selected treatment electrodes to cause ablation in a preselected location in the wall of the heart chamber.

11. The ablation apparatus of claim 8, wherein the treatment electrodes are multiplexed.

12. The ablation apparatus of claim 8, wherein the member is secured distal end of the catheter for insertion into and removal from the heart chamber.

13. The ablation apparatus of claim 8, wherein the member includes a deposition of ions to improve RF and thermal energy conductivity.

14. The ablation apparatus of claim 8, wherein the plurality of treatment electrodes are positioned in a spaced apart relationship within the member.

15. An endocardial ablation apparatus for introduction into a heart chamber formed by a wall, comprising:
- an inflatable, flexible porous membrane adapted to receive an electrolytic solution and become inflated to substantially conform a conductive surface of the membrane to the wall of the heart chamber;
- a membrane support surrounded by the membrane including a sealed proximal end and a sealed distal end, each end having an aperture formed therein defining a central lumen in the membrane support that permits blood flow through the support member and heart chamber, the membrane support being attached to the membrane and expanded to a non-distensible state when the membrane is inflated;
- a catheter for introducing the membrane and membrane support into the heart chamber in a non-expanded state, the catheter including a lumen for delivering an electrolytic solution to the membrane to inflate the membrane;
- a plurality of treatment electrodes defining a circuit formed on an exterior surface of the membrane support:
- an RF power source coupled to the treatment electrodes; and
- a source of electrolytic solution coupled to the membrane.

16. The ablation apparatus of claim 15, wherein the membrane further comprises electrical resources for acquiring electrical data from the heart and providing electrical function feedback to the RF power source which then supplies a therapeutic output to selected treatment electrodes of the plurality.

17. The ablation apparatus of claim 15, wherein the membrane further comprises a plurality of MAP electrodes coupled to the RF power source.

18. The ablation apparatus of claim 17, wherein the MAP electrodes are positioned on the conductive surface of the membrane.

19. The ablation apparatus of claim 15, wherein the membrane and the membrane support include a plurality of apertures appropriately spaced to permit blood flow to the superior vena cava, the inferior vena cava, and the tricuspid valve annulus.

20. The ablation apparatus of claim 15, further comprising:
- a ground pad electrode attached to an exterior surface of a patient.

21. The ablation apparatus of claim 15, where the apparatus operates in a bipolar mode.

22. The ablation apparatus of claim 16, wherein the electrical resources includes members for recording mapping potentials encountered by the treatment electrodes.

23. The ablation apparatus of claim 15, wherein the electrical resources include devices for supplying a predetermined voltage at a predetermined frequency to selected treatment electrodes to cause ablation in a preselected location in the wall of the heart chamber.

24. The ablation apparatus of claim 15, wherein the membrane includes a conductive surface which is adapted to substantially conform to the wall of the atrium.

25. The ablation apparatus of claim 15, wherein the circuit is a flexible circuit.

26. The ablation apparatus of claim 15, further comprising:
- attachment members positioned on the catheter distal end and attaching to the membrane or membrane support.

27. The ablation apparatus of claim 15, wherein the plurality of treatment electrodes are multiplexed.

28. The ablation apparatus of claim 15, wherein the circuit is multiplexed.

29. The ablation apparatus of claim 15, wherein the membrane and the membrane support are rolled around the catheter distal end for removal from the heart chamber.

30. The ablation apparatus of claim 15, wherein the circuit includes one or more impedance monitors.

31. The ablation apparatus of claim 15, wherein the circuit includes one or more temperature monitors.

32. The ablation apparatus of claim 15, wherein the circuit includes one or more devices to monitor circuit continuity.

33. The ablation apparatus of claim 15, wherein the circuit includes a plurality of segments.

34. The ablation apparatus of claim 15, wherein the membrane includes a deposition of ions to improve RF and thermal energy conductivity.

35. The ablation apparatus of claim 15, wherein the conductive surface is coated with an anticoagulating material.

36. The ablation apparatus of claim 15, wherein the membrane support is made of Mylar.

37. The ablation apparatus of claim 15, wherein the plurality of treatment electrodes are positioned between the membrane support and the surrounding membrane.

38. The ablation apparatus of claim 15, wherein the plurality of treatment electrodes are positioned in the membrane in a spaced apart relationship from the conductive surface.

39. An endocardial ablation apparatus for introduction into a heart chamber formed by a wall, comprising:
- an inflatable, flexible porous membrane adapted to receive an electrolytic solution and become inflated to substantially conform a conductive surface of the membrane to the wall of the heart chamber;
- a membrane support surrounded by the membrane including a central lumen for permitting blood flow through the membrane support and the heart chamber, the membrane support being attached to the membrane and expanded to a non-distensible state when the membrane is inflated;
- a catheter for introducing the membrane and support member into the heart chamber in a non-expanded state, the catheter including a lumen for delivering an electrolytic solution to the membrane to inflate the membrane;
- a plurality of treatment electrodes positioned between the membrane support and the surrounding membrane, at least a portion of the plurality of treatment electrodes including an insulator formed on a surface of the electrode adjacent to the membrane;
- an RF power source coupled to the treatment electrodes; and
- a source of electrolytic solution coupled to the membrane.

40. The ablation apparatus of claim 39, wherein the plurality of treatment electrodes is formed on an exterior surface of the membrane support wall.

41. The ablation apparatus of claim 39, wherein the membrane further comprises electrical resources for acquiring electrical data from the heart and providing electrical function feedback to the RF power source which then supplies a therapeutic output to selected treatment electrodes of the plurality.

42. The ablation apparatus of claim 39, wherein the membrane further comprises a plurality of MAP electrodes coupled to the RF power source.

43. The ablation apparatus of claim 39, wherein the MAP electrodes are positioned on the conductive surface of the membrane.

44. The ablation apparatus of claim 42, wherein the membrane support includes a proximal and a distal end, each end being sealed.

45. The ablation apparatus of claim 39, wherein the membrane and the membrane support include a plurality of apertures appropriately spaced to permit blood flow to the superior vena cava, the inferior vena cava, and the tricuspid valve annulus.

46. The ablation apparatus of claim 39, further comprising:

a ground pad electrode attached to an exterior surface of a patient.

47. The ablation apparatus of claim 39, wherein the apparatus operates in a bipolar mode.

48. The ablation apparatus of claim 41, wherein the electrical resources includes members for recording mapping potentials encountered by the treatment electrodes.

49. The ablation apparatus of claim 41, wherein the electrical resources include devices for supplying a predetermined voltage at predetermined frequency to selected treatment electrodes to cause ablation in a preselected location in the wall of the heart chamber.

50. The ablation apparatus of claim 39, wherein the membrane includes a conductive surface which is adapted to substantially conform to the wall of the atrium.

51. The ablation apparatus of claim 39, wherein the membrane includes a deposition of ions to improve conductivity.

52. The ablation apparatus of claim 39, wherein the conductive surface is coated with an anticoagulating material.

53. The ablation apparatus of claim 39, wherein the membrane support is made of Mylar.

54. The ablation apparatus of claim 39, wherein the plurality of treatment electrodes are in a spaced apart relationship relative to the conductive surface.

* * * * *